(12) United States Patent
Vanbenschoten et al.

(10) Patent No.: US 7,172,008 B2
(45) Date of Patent: Feb. 6, 2007

(54) HOOK FASTENERS AND METHODS OF MAKING THE SAME

(75) Inventors: Brian J. Vanbenschoten, Rochester, NH (US); Ernesto S. Tachauer, Bedford, NH (US); Wallace L. Kurtz, Jr., Lunenburg, MA (US); Heidi S. Tremblay, Ft. Launderdale, FL (US); Paul A. Dandurand, Manchester, NH (US); William P. Clune, Northwood, NH (US); Alexander J. Neeb, Alpharetta, GA (US); Joseph E. Pierce, Appleton, WI (US); Richard J. Schmidt, Roswell, GA (US); Richard W. Tanzer, Neenah, WI (US)

(73) Assignee: Velcro Industries B.V., Curacao (AN)

( * ) Notice: Subject to any disclaimer, the term of this patent is extended or adjusted under 35 U.S.C. 154(b) by 0 days.

(21) Appl. No.: 10/666,304

(22) Filed: Sep. 18, 2003

(65) Prior Publication Data
US 2005/0060849 A1    Mar. 24, 2005

(51) Int. Cl.
*B29C 65/48* (2006.01)
*B29C 47/06* (2006.01)

(52) U.S. Cl. ............... 156/544; 156/244.22; 264/45.9; 264/167

(58) Field of Classification Search .............. None
See application file for complete search history.

(56) References Cited

U.S. PATENT DOCUMENTS

| | | | |
|---|---|---|---|
| 3,462,332 A | 8/1969 | Goto | |
| 3,464,094 A * | 9/1969 | Mates | 24/443 |
| 3,773,882 A * | 11/1973 | Schrenk | 264/173.12 |
| 3,849,174 A * | 11/1974 | Ancker | 427/365 |
| 3,884,606 A * | 5/1975 | Schrenk | 425/133.5 |
| 4,248,824 A | 2/1981 | Hattop | |
| 4,259,133 A | 3/1981 | Yagi | |
| 4,322,875 A * | 4/1982 | Brown et al. | 24/447 |
| 4,536,362 A | 8/1985 | Donaldson | |
| 4,539,169 A | 9/1985 | Nixon et al. | |
| 4,540,537 A | 9/1985 | Kamp | |
| 4,592,938 A * | 6/1986 | Benoit | 428/35.5 |
| 4,661,396 A | 4/1987 | Andorf et al. | |
| 4,682,691 A * | 7/1987 | Spiering | 206/373 |
| 4,770,917 A * | 9/1988 | Tochacek et al. | 428/95 |
| 4,822,539 A | 4/1989 | Tilman et al. | |
| 4,839,131 A | 6/1989 | Cloeren | |
| 4,877,672 A | 10/1989 | Shreiner | |

(Continued)

FOREIGN PATENT DOCUMENTS

EP     0 780 066 B1    4/2002

(Continued)

*Primary Examiner*—Mark Eashoo
(74) *Attorney, Agent, or Firm*—Fish & Richardson P.C.

(57) ABSTRACT

A method of making a touch fastener includes coextruding, side-by-side, a plurality of lanes of polymeric material to form a sheet-form base. The sheet-sheet form base includes a lane of a first polymeric material disposed between two lanes of a second polymeric material, the second polymeric material is different from the first polymeric material. The method further includes molding a plurality of discrete fastener element stems extending outwardly from and integral with the sheet-form base in each of the two lanes of the second polymeric mateial and forming engageable heads on the stems.

15 Claims, 24 Drawing Sheets

U.S. PATENT DOCUMENTS

| | | | | |
|---|---|---|---|---|
| 4,931,343 A * | 6/1990 | Becker et al. | ................ | 428/95 |
| 5,017,118 A | 5/1991 | Looman et al. | | |
| 5,053,028 A | 10/1991 | Zoia et al. | | |
| 5,110,530 A | 5/1992 | Havens | | |
| 5,145,544 A | 9/1992 | Leseman et al. | | |
| 5,173,141 A | 12/1992 | Leseman et al. | | |
| 5,216,787 A | 6/1993 | Custer et al. | | |
| 5,260,015 A * | 11/1993 | Kennedy et al. | ............ | 264/167 |
| 5,273,506 A * | 12/1993 | Dawson, Jr. | ................ | 482/104 |
| 5,279,604 A | 1/1994 | Robertson et al. | | |
| 5,441,687 A * | 8/1995 | Murasaki et al. | ........... | 264/167 |
| 5,549,591 A | 8/1996 | Landvogt | | |
| 5,669,120 A * | 9/1997 | Wessels et al. | ................ | 24/446 |
| 5,725,928 A * | 3/1998 | Kenney et al. | ............. | 428/100 |
| 5,744,080 A * | 4/1998 | Kennedy et al. | ............ | 264/167 |
| 5,800,760 A * | 9/1998 | Takizawa et al. | ........... | 264/167 |
| 5,851,467 A * | 12/1998 | Murasaki | .................... | 264/167 |
| 6,008,294 A * | 12/1999 | Bonekamp et al. | ........... | 525/98 |
| 6,035,498 A | 3/2000 | Buzzell et al. | | |
| 6,060,009 A * | 5/2000 | Welygan et al. | ............ | 264/167 |
| 6,066,281 A * | 5/2000 | Provost | ..................... | 264/167 |
| 6,106,922 A * | 8/2000 | Cejka et al. | ................ | 428/120 |
| 6,174,476 B1 * | 1/2001 | Kennedy et al. | ............ | 264/167 |
| RE37,095 E * | 3/2001 | Glorioso et al. | ............. | 521/79 |
| 6,205,623 B1 | 3/2001 | Shepard et al. | | |
| 6,221,483 B1 * | 4/2001 | Hilston et al. | .............. | 428/343 |
| 6,463,634 B1 | 10/2002 | Naohara et al. | | |
| 6,481,063 B2 | 11/2002 | Shepard et al. | | |
| 6,538,050 B1 * | 3/2003 | Weilandt et al. | ............. | 523/219 |
| 6,540,863 B2 * | 4/2003 | Kenney et al. | ........ | 156/244.25 |
| 6,588,073 B1 | 7/2003 | Zoromski et al. | | |
| 6,669,887 B2 * | 12/2003 | Hilston et al. | ......... | 264/173.15 |
| 6,692,674 B1 * | 2/2004 | Kurtz et al. | ................ | 264/167 |
| 6,827,893 B2 * | 12/2004 | Clune | ........................ | 264/129 |
| 6,896,759 B2 * | 5/2005 | Fujisawa et al. | ....... | 156/244.18 |
| 2001/0000547 A1 | 5/2001 | Tachauer et al. | | |
| 2001/0038161 A1 | 11/2001 | Kenney et al. | | |
| 2002/0022108 A1 * | 2/2002 | Krantz et al. | ............... | 428/100 |
| 2003/0015819 A1 * | 1/2003 | Levitt et al. | ................ | 264/167 |
| 2003/0034583 A1 | 2/2003 | Provost | | |
| 2004/0045142 A1 * | 3/2004 | Buzzell et al. | ............... | 24/452 |
| 2004/0187275 A1 * | 9/2004 | Kennedy et al. | ............... | 24/445 |
| 2004/0222551 A1 * | 11/2004 | Provost et al. | ............. | 264/145 |

FOREIGN PATENT DOCUMENTS

| | | |
|---|---|---|
| JP | HEI-8-187113 | 7/1996 |
| WO | WO 97/25892 | 7/1997 |
| WO | WO 98/32349 | 7/1998 |
| WO | WO 01/67911 A2 | 9/2001 |

* cited by examiner

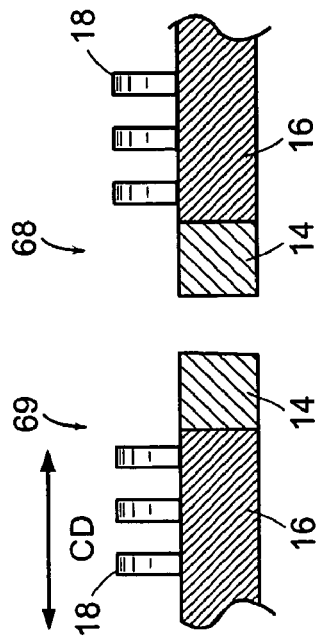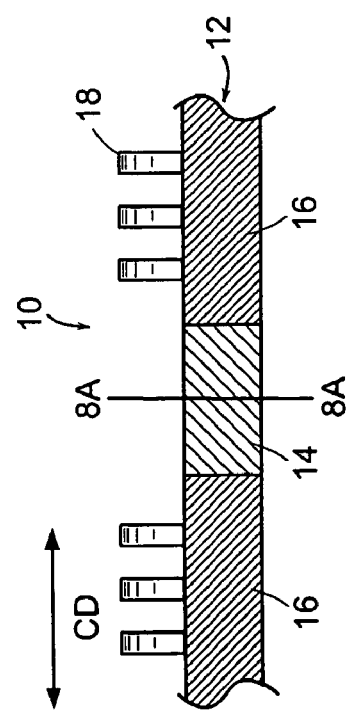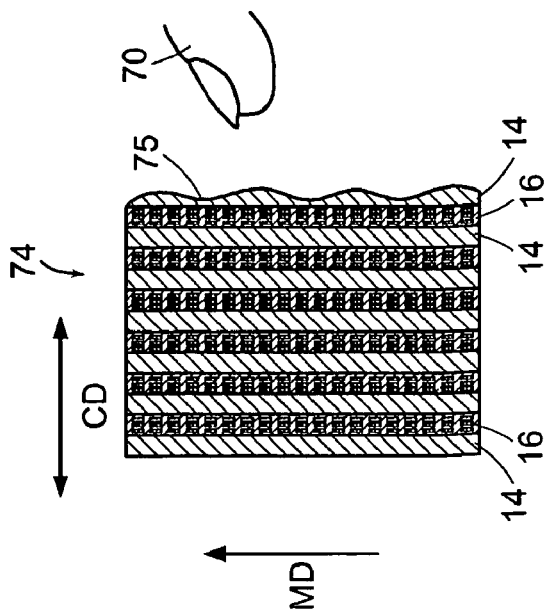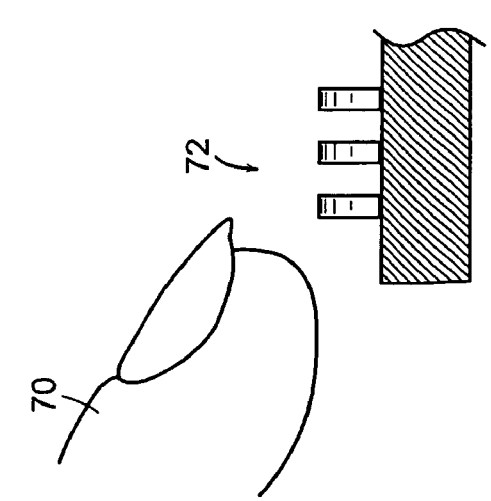

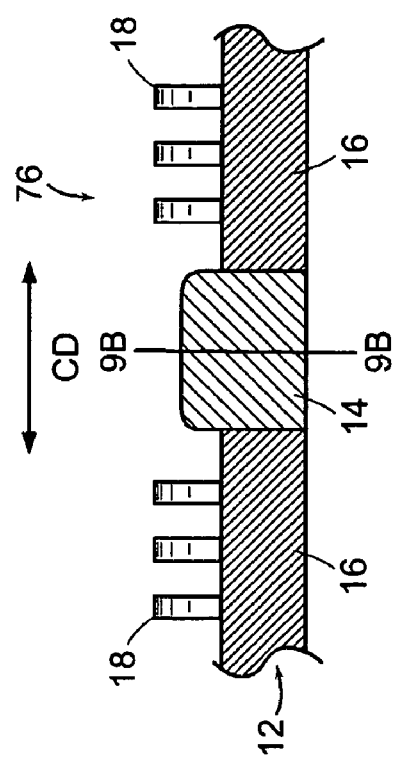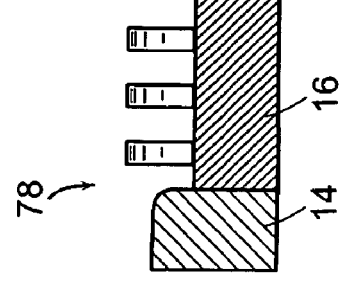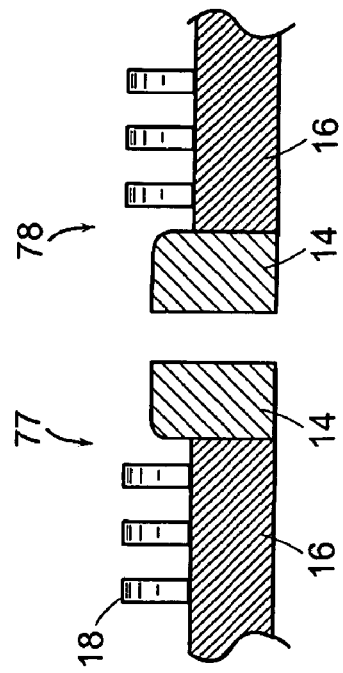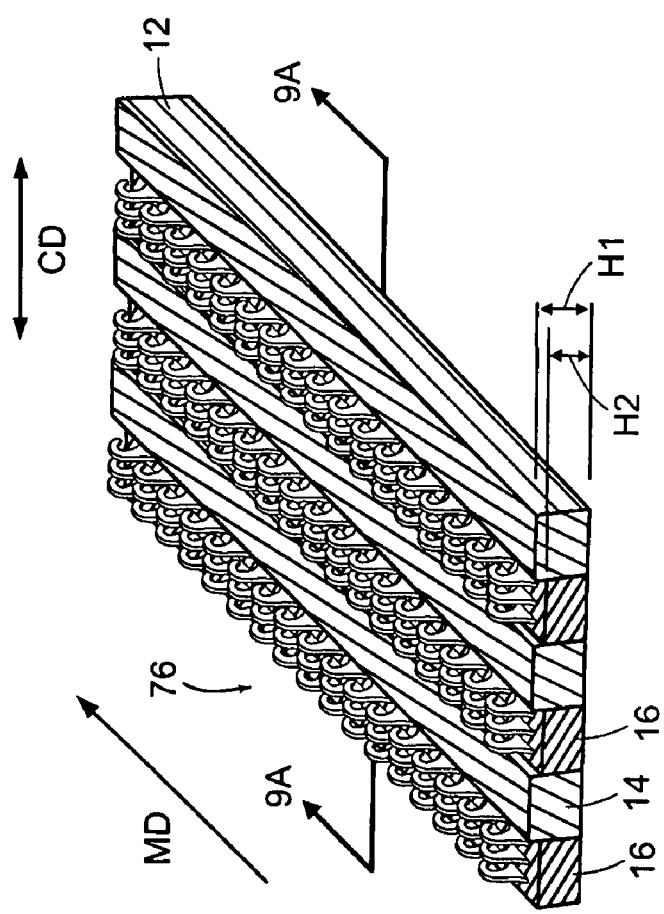

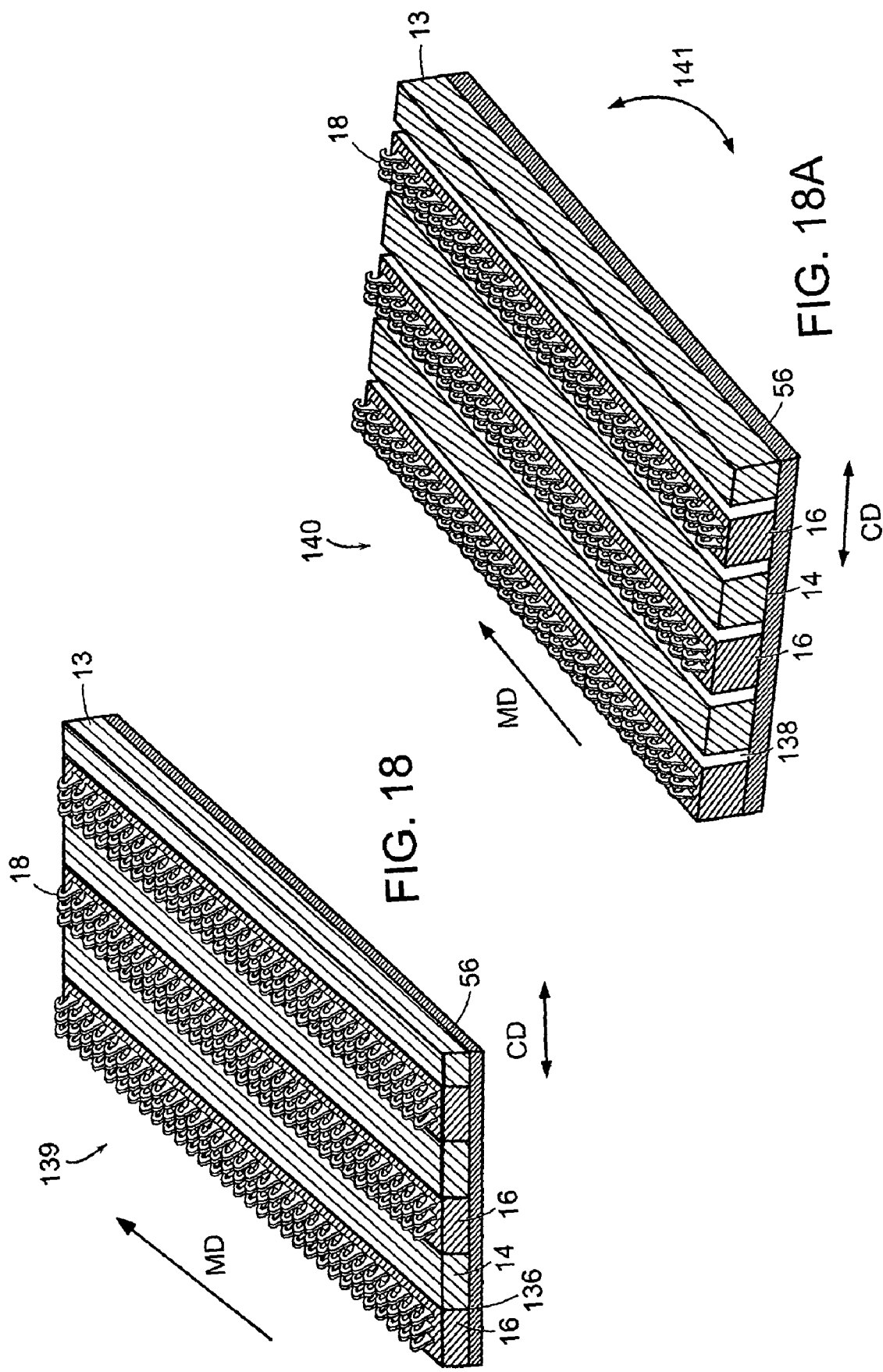

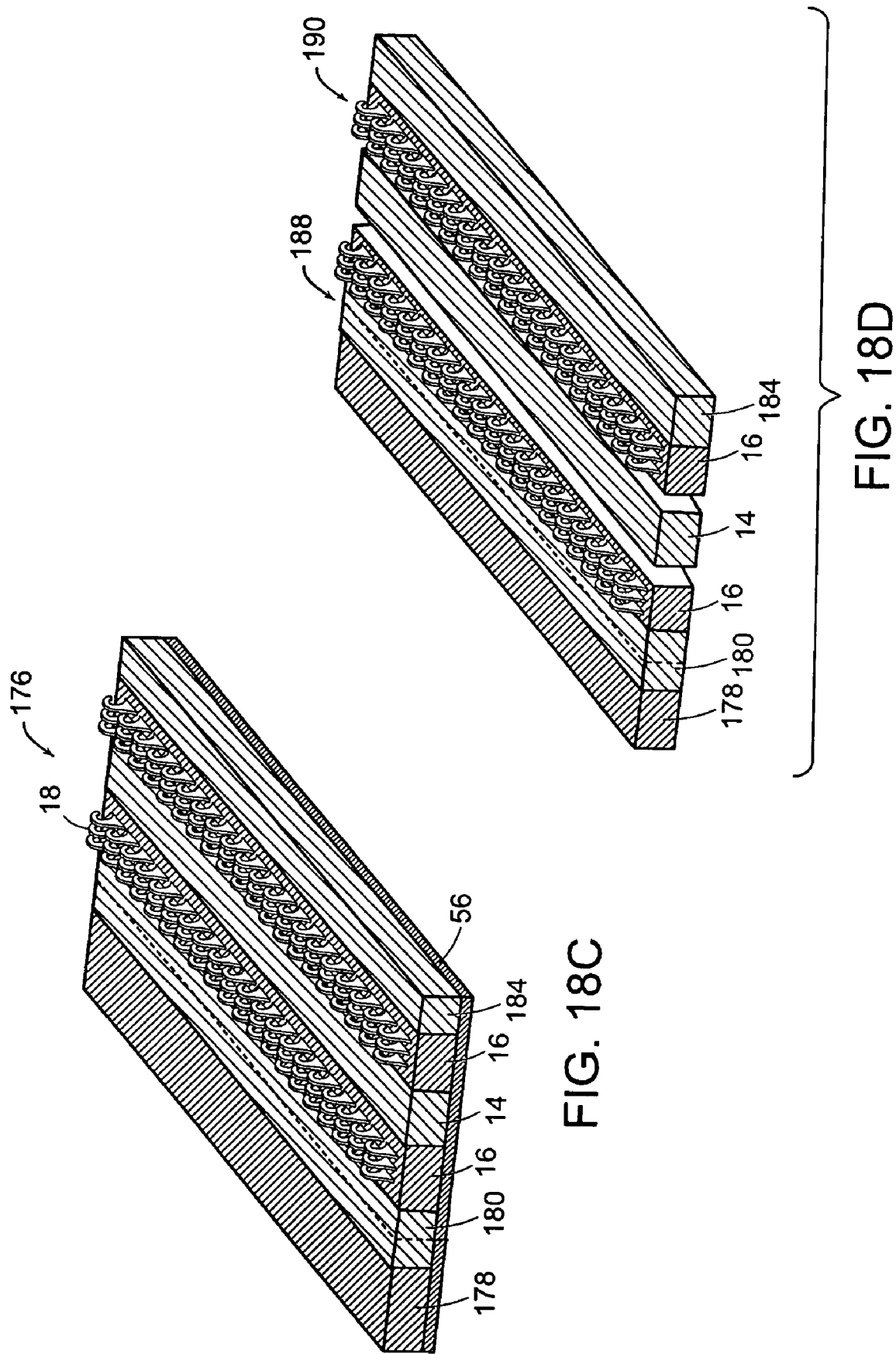

HOOK FASTENERS AND METHODS OF MAKING THE SAME

TECHNICAL FIELD

This invention relates to fasteners, in particular to hook and loop type fasteners.

BACKGROUND

Arrays of molded male fastener elements, e.g., hooks are often formed integrally with a sheet-form base, to provide a sheet-form fastener component. This component can then be engaged with female fastener elements to form a "hook and loop" fastener. It is generally desirable that the fastener elements have good strength and toughness, so as to provide strong engagement during repeated use of the fastener. In some cases, it is also desirable that the sheet-form base be relatively soft and flexible, e.g., to allow the base to flex with a fabric article to which it is attached and to prevent the edges of the sheet-form component from causing discomfort to the wearer.

Fastener products such as hook and loop type fasteners find extensive use in personal care absorbent articles including, but not limited, to diapers, training pants, disposable swimwear, incontinence garments and pads, and sanitary napkins.

SUMMARY

One aspect of the invention features, in general, a method of making a touch fastener. The method includes coextruding, side-by-side, a plurality of lanes of polymeric material to form a sheet-form base. The sheet-sheet form base includes a lane of a first polymeric material disposed between two lanes of a second polymeric material, the second polymeric material is different from the first polymeric material. The method further includes molding a plurality of discrete fastener element stems extending outwardly from and integral with the sheet-form base in each of the two lanes of the second polymeric mateial and forming engageable heads on the stems.

In some implementations, the method further includes molding discrete fastener element stems extending outwardly from and integral with the sheet-form base in the lane of the first polymeric material. Engageable heads may be formed on the discrete fastener element stems extending outwardly from and integral with the sheet-form base in the lane of the first polymeric material. The shape of the fastener elements extending from the first polymeric material may be different than the shape of the fastener elements extending from the second polymeric material. The height of the elements extending from the first and second polmeric material may be different. A tie layer may be disposed between the lanes of the first and second polymeric material. In some embodiments, the sheet-form base includes more than three lanes and the method further includes arranging the lanes so that lanes of the first polymeric material alternate with lanes of the second polymeric material. In other implementations, the method further includes coextruding a polymeric layer during the coextruding of the side-by-side polymeric lanes, the polymeric layer is disposed on the side opposite the molded fastener element stems. In some embodiments, the method further includes bringing in a polymeric layer as pre-form during the coextruding of the side-by-side polymeric lanes, the polymeric layer is disposed on the side opposite the molded fastener element stems. In yet other embodiments, the method further includes bonding a polymeric layer of material to the sheet-form base opposite the fastener element stems. The coextruding, molding, forming engageable heads and bonding the polymeric layer may be performed continuously.

Another aspect of the invention features, in general, a touch fastener that includes a sheet-form base having a plurality of lanes of polymeric material including a lane of a first polymeric material disposed between two lanes of a second polymeric material, the second polymeric material different from the first polymeric material. Each of the lanes of the second polymeric material have a plurality of discrete fastener elements comprising stems integrally molded with and extending outwardly from the sheet-form base.

In some implementations, fastener elements extend outwardly from and integral with the sheet-form base in the lane of the first polymeric material. The first polymeric material may be, for example, an elastomer. The touch fastener may be part of, for example, a personal care absorbent product.

Another aspect of the invention features, in general, a touch fastener that includes a plurality of lanes of polymeric material, forming a sheet-form base. The sheet-form base includes a lane of a first polymeric material and a lane of a second polymeric material, the second polymeric material includes a foam. Extending outwardly from and integral with the sheet-form base in lanes of the first polymeric material is a plurality of discrete fastener elements including stems.

In some implementations, fastener elements extend outwardly from and integral with the sheet-form base in the lane of the second polymeric material that includes a foam. The second polymeric material may be, for example, a foamed thermoplastic, a foamed thermoplastic elastomer or a formed thermoset. In other embodiments, the first and second polymeric material alternate. A polymeric layer may be bonded to the sheet-form base on the side opposite the fastener elements. The touch fastener may be part of, for example, a personal care absorbent product.

Another aspect of the invention features, in general, a method of making a touch fastener that includes coextruding, side-by-side, a plurality of lanes of polymeric material to form a sheet-form base. The method further includes molding a plurality of discrete fastener element stems extending outwardly from and integral with the sheet-form base in lanes of the first polymeric material and forming engageable heads on the stems. The sheet-form base includes a lane of a first polymeric material and a second polymeric material, the second polymeric material includes a foam.

In some implementations, the method further includes molding discrete fastener element stems extending outwardly from and integral with the sheet-form base in the lane of the second polymeric material that includes a foam. Engageable heads may be formed on the stems. A tie layer may be disposed between the first and second polymeric materials. The foam may be formed by a chemical foaming agent or by injecting gas into the second lane. The foam may be a thermoset.

Another aspect of the invention features, in general, a method of making a touch fastener that includes bonding a plurality of discrete side-by-side lanes of polymeric material together to form a sheet-form base, molding a plurality of discrete fastener element stems extending outwardly from and integral with the sheet-form base in lanes of the first polymeric material and forming engageable heads on the stems. The sheet-form base includes a lane of a first polymeric material and a second polymeric material, the second polymeric material includes a foam.

Another aspect of the invention features, in general, a touch fastener, including a plurality of lanes and an adjoining layer of polymeric material to form a sheet-form base, the adjoining layer is below and integral with the plurality of lanes. The sheet-form base includes a lane of a first polymeric material disposed between two lanes of a second polymeric material, the second polymeric material different from the first polymeric material. Extending outwardly from and integral with the sheet-form base, opposite the adjoining layer, in each of the two lanes of the second polymeric material is a plurality of fastener elements. The touch fastener may be part of, for example, a personal care absorbent product.

Another aspect of the invention features, in general, a method of making a touch fastener that includes forming a composite polymeric sheet from at least two different polymeric materials forming corresponding portions of the sheet and defining a boundary therebetween. The method further includes forming a plurality of discrete fastener elements extending outwardly from at least one exposed surface of the composite sheet, stretching the formed sheet sufficiently to cause one of the portions to permanently deform to a greater extent than the other of the portions and reducing stretch of the sheet to allow differences in stretch response between the two portions to locally distort a shape of the sheet.

In some implementations, the two different polymeric materials may be coextruded side-by-side, forming a plurality of lanes, including a lane of a first polymeric material disposed between two lanes of a second polymeric material.

Another aspect of the invention features, in general, a method of making a touch fastener that includes coextruding, side-by-side, a plurality of lanes of at least two different polymeric materials, forming a contiguous polymeric sheet. The method further includes forming a plurality of discrete fastener elements extending outwardly from at least one portion of the sheet, forming an adjoining layer of polymeric material and bonding the adjoining layer to the formed polymeric sheet on a side opposite the fastener elements, forming a composite. Finally, the method further includes stretching the formed composite sufficiently in a lateral direction to cause at least one lane of the polymeric sheet to separate from an adjacent lane.

In some implementations, the stretching is performed under the application of heat. The adjoining layer may be adhesive coated. In some embodiments, the polymeric material of a lane or lanes may contain an additive to aid, for example, in the seperation of the lanes upon stretching.

Another aspect of the invention features, in general, a touch fastener that includes an undulating composite polymeric sheet with local peaks and troughs. The composite polymeric sheet includes at least two different polymeric materials featuring different degrees of stress. The polymeric materials defining different portions of the sheet and defining a boundary therebetween and extending outwardly from at least one surface of the composite a plurality of molded elements. The touch fastener may be part of, for example, a personal care absorbent product.

In some implementations, engagaeable heads are included on the stems. In other implementations, the molded elements extend from both peaks and troughs in the sheet.

Advantages of the invention may include, for example, providing a stretchable fastener that has strong engagement during repeated use. Other advantages may include, for example, providing a fastener that is relatively soft and flexible, for example, to allow the base to flex with a fabric article to which it is attached and to prevent the edges of the sheet-form component from causing discomfort to the wearer.

The details of one or more embodiments of the invention are set forth in the accompanying drawings and the description below. Other features, and advantages of the invention will be apparent from the description and drawings and from the claims.

DESCRIPTION OF DRAWINGS

FIG. 8 is an enlarged cross-sectional view of a portion of the embodiment shown in FIG. 1, taken along line 1A—1A, showing cut line 8A—8A.

FIG. 8A is an enlarged cross-sectional view of a portion of the embodiment shown in FIG. 8 after cutting along line 8A—8A.

FIG. 8B is an enlarged cross-sectional view of another portion of the embodiment shown in FIG. 8 after cutting along line 8A—A.

FIG. 8C shows a prior art fastener with a potentially sharp edge.

FIG. 8D shows a top view of a fastener having a non-linear cut line.

FIG. 9 is a perspective view of a fastener including height-differentiation.

FIG. 9A is an enlarged cross-sectional view of a portion of the fastener shown in FIG. 9, taken along line 9A—9A.

FIG. 9B shows a portion of the fastener shown in FIG. 9A after cutting along line 9B—9B.

FIG. 9C shows a portion of the fastener shown in FIG. 9A.

FIG. 18 shows a perspective view of a fastener.

FIG. 18A shows the fastener of FIG. 18 after stretching in the cross machine direction.

FIG. 18C shows a perspective view of a fastener.

FIG. 18D shows the fastener of FIG. 18C after removal of the adjoining layer.

DETAILED DESCRIPTION

Figure 1:
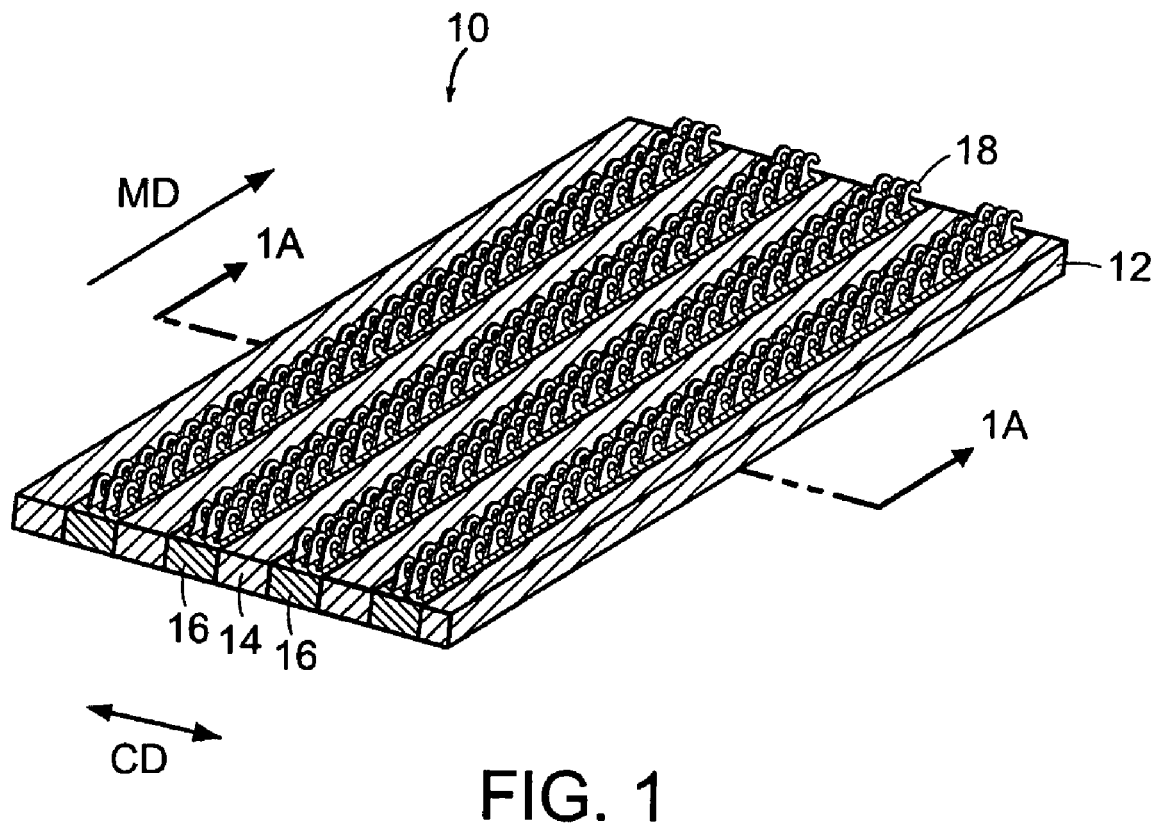
FIG. 1 is a perspective view of a fastener according to one embodiment.

FIG. 1 shows a sheet-form fastener 10, including a plurality of coextruded, side-by-side lanes extending longitudinally in the machine direction (MD), forming a sheet-form base 12. The sheet-form base 12 includes lanes 14 of a first polymeric material disposed in an alternating arrangement between lanes 16 of a second, different polymeric material. Molded integrally with and extending outwardly from the sheet-form base 12 in each of the lanes 16 of the second polymeric material are a plurality of fastener hooks 18, as shown in detail in FIG. 1A. Fastener products like these are useful, for example, for creating safe, skin-friendly products. They are also useful, for example, in creating better engaging products with greater stretch in the cross-machine direction (CD). Furthermore, hybrid fasteners with unusual combinations of properties can be engineered which gives the end user more design freedom. For example, skin-friendly products can be created in combination with more aggressive, better engaging hooks. Polymeric material pairs for lanes 14 and 16 can include, for example, ABS/polycarbonate, polypropylene/thermoplastic olefin, ABS (acrylonitrile butadiene styrene copolymer)/PVC (polyvinyl chloride), polypropylene/styrenic block copolymer elastomer and polypropylene/polypropylene-based thermoplastic elastomer vulcanizate. For example, a suitable material for lane 14 is a polypropylene-based thermoplastic elastomer vulcanizate (e.g., SANTOPRENE® elastomer available from Advanced Elastomer Systems, Akron, Ohio) and a suitable material for lane 16 is polypropylene. Different colors may be used, for example, to differentiate the lanes and to denote the function of each lane. Other additives that improve function or aesthetics may also be used. For example, glow in the dark additives, moisture-detecting additives and thermochromic additives may be used in the sheet-form fastener.

Figure 2:
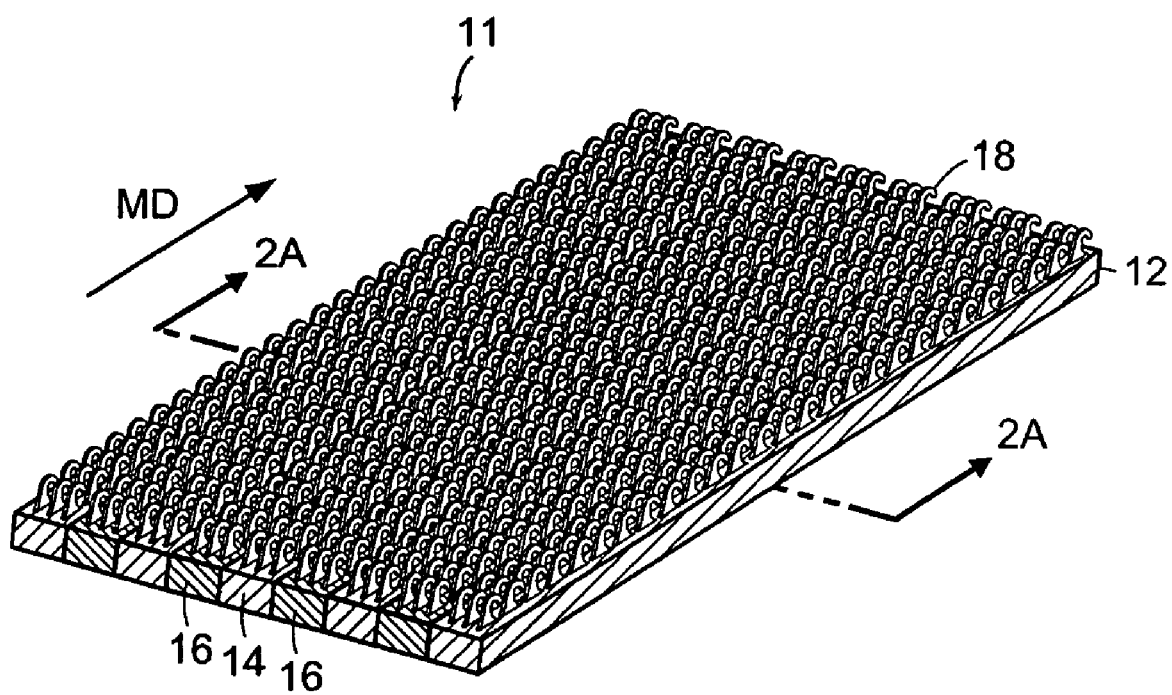
FIG. 2 is a perspective view of an alternative embodiment.
Figure 2A:
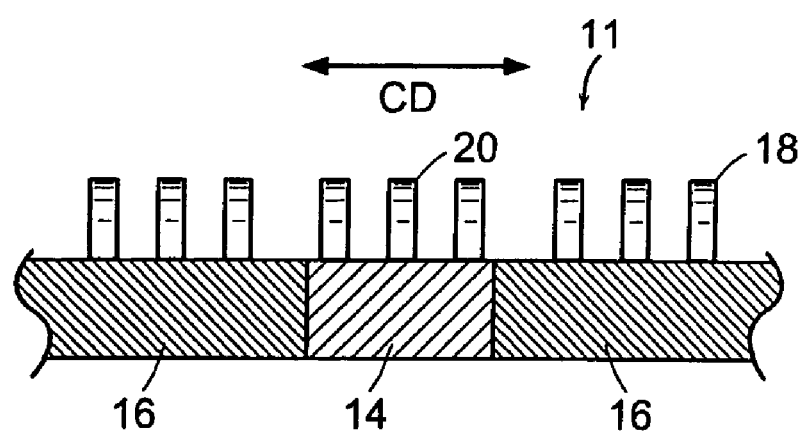
FIG. 2A is an enlarged cross-sectional view of a portion of the fastener shown in FIG. 2, taken along line 2A—2A.

FIG. 2 shows a sheet-form fastener 11, where all lanes of the first and second polymeric materials include a plurality of integrally molded fastener hooks 18 and 20. Thus, hooks 18 are formed of the second polymeric material, while hooks 20 are formed of the first polymeric material. The geometry of the hooks can be different in different lanes. In some cases it may be advantageous to have specific hooks on specific regions of the fastener to balance function and safety. For example, aggressive palm-tree hooks can be used in hard lanes and skin-friendly, flat-topped hooks in soft lanes. A fastener like this would have high peel strength, but would also be skin-friendly. This product would be useful, for example, in a diaper application. Another example would be to put flat-topped hooks in lanes of a relatively hard material and palm-tree hooks in the other lane of a relatively hard material. Fastener such as this would be useful, for example, when both high shear and high peel are needed. FIG. 2A shows an enlarged cross-sectional view. Suitable polymers and polymer pairs include those discussed above with reference to FIG. 1.

Figure 3:
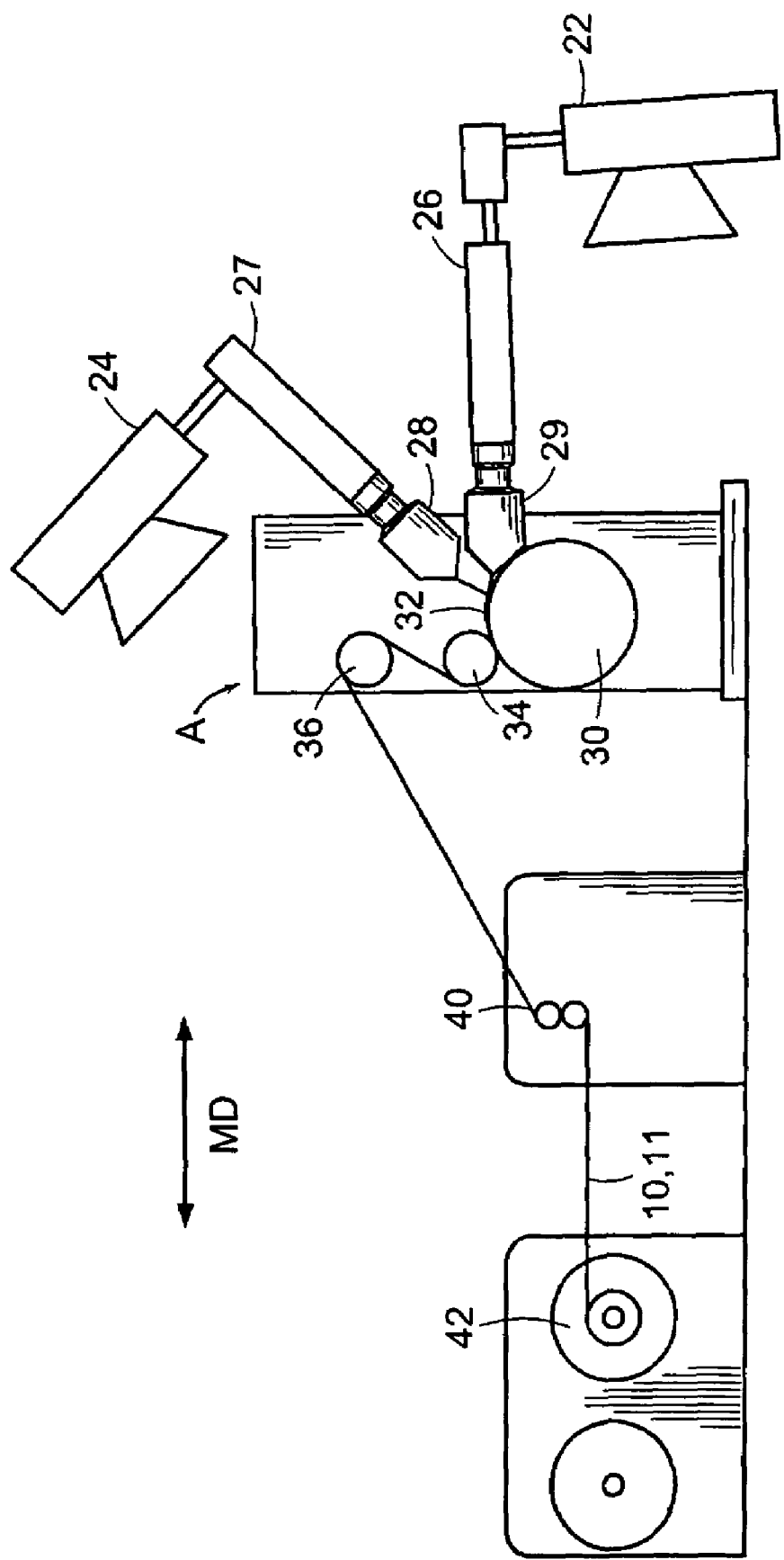
FIG. 3 is a diagrammatic view of a process for making a fastener according to one embodiment.
Figure 3A:
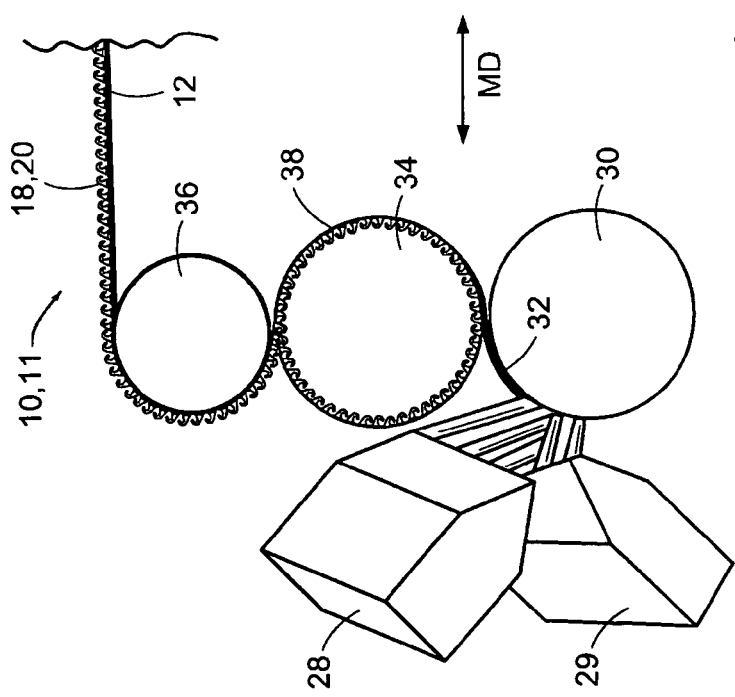
FIG. 3A is an enlarged diagrammatic view of the portion of the process of FIG. 3 shown in box A.

FIG. 3 illustrates a suitable process for forming the sheet-form fasteners shown in FIG. 1 and FIG. 2. As shown in FIG. 3, extruder 22 and extruder 24 pump their respective polymeric materials through their respective die connectors 26 and 27 and through their respective dies 28 and 29, onto rotating roll 30 to form a web 32 that will define the sheet-form base 12 in the finished product (e.g., fastener 10 or 11). The die for the first polymeric material is offset from the die for the second polymeric material so that when the materials are coextruded, a plurality of side-by-side lanes are created. The web 32 is pulled through the nip between roll 30 and a hook-forming roll 34, forming hooks extending from the web, and stripped from hook-forming roll 34 by passing the web 32 around a stripping roll 36. As shown in FIG. 3A, hook-forming roll 34 includes hook-forming cavities 38. Hook-forming roll 34 is formed of a plurality of etched plates, e.g., as described in Fischer U.S. Pat. No. 4,775,310, the entire disclosure of which is incorporated by reference herein. Additional processing can be applied at nip roll 40. For example, additional processing may include forming fiber-engaging plate portions at the distal end of the hooks as described in U.S. Pat. No. 5,953,797, the disclosure of which is incorporated by reference herein. The finished sheet-form fastener 10 or 11 is collected at a wind-up roll 42.

Figure 4A:
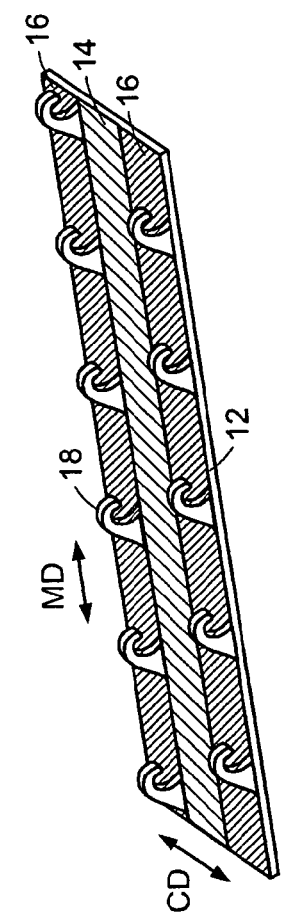
FIG. 4A is a perspective view of a fastener made by the process shown in FIG. 4.
Figure 4:
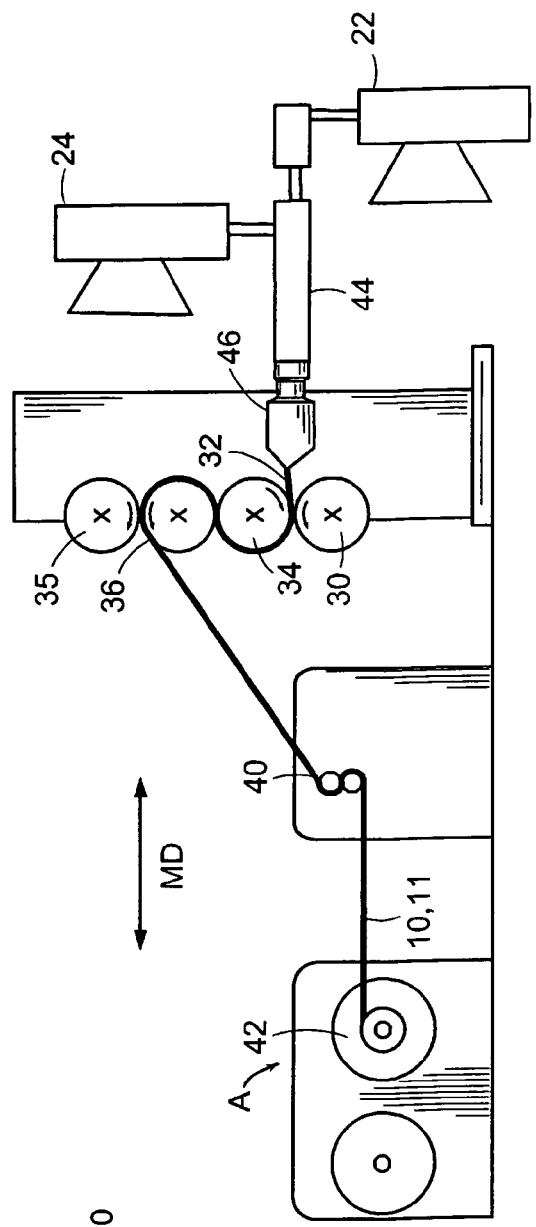
FIG. 4 is a diagrammatic view of a process for making a fastener according to an alternative embodiment.

FIG. 4 illustrates a suitable alternative process for forming the sheet-form fasteners shown in FIG. 1 and FIG. 2. This process is similar to that described with reference to FIG. 3, except the two extruders 22 and 24 are connected via a stream connector 44. Material passes through stream connector 44 into die splitter 46. Exiting the die splitter 46 are alternating, side-by-side lanes which form the web 32. The fastener product is stripped from hook-forming roll 34 by passing the web 32 between stripping rolls 35 and 36. FIG. 4A shows a portion of a possible product resulting from the process. Typically, the base is, for example, from about 0.001 to about 0.01 inch (about 0.025 mm to about 0.25 mm) thick, the hooks extend, for example, from about 0.005 to about 0.1 inch (about 0.127 mm to about 2.54 mm) above the base and the hooks have a density, for example, of about 250 to about 4000 hooks/inch$^2$ (about 39 to about 620 hooks/cm$^2$). Other suitable processes may be used to form the fastener products. U.S. Pat. No. 6,432,339, the entire disclosure of which is incorporated by reference herein, describes another process that would be suitable if modified to include coextrusion.

Figure 4B:
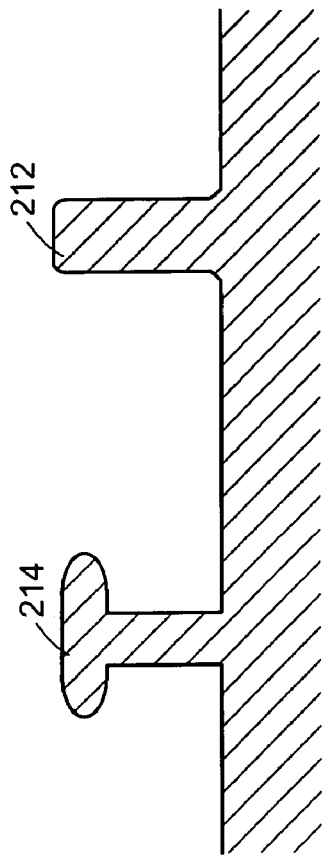
FIG. 4B is a diagrammatic view of a process for making a fastener according to an alternative embodiment.
Figure 4C:
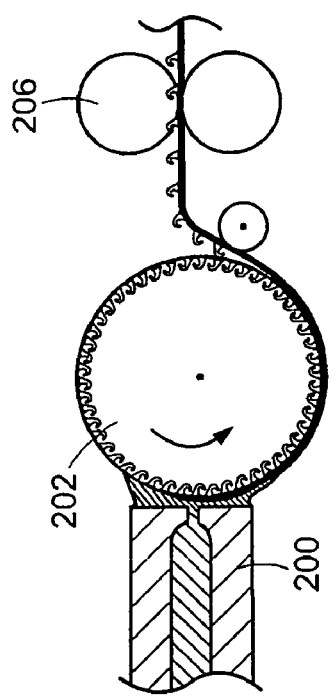
FIG. 4C is a cross-sectional view showing other hook shapes that can be produced by the process shown in FIG. 4B.
Figure 4D:
FIG. 4D is a cross-sectional view showing other hook shapes that can be produced by the process shown in FIG. 4B.
Figure 4E:
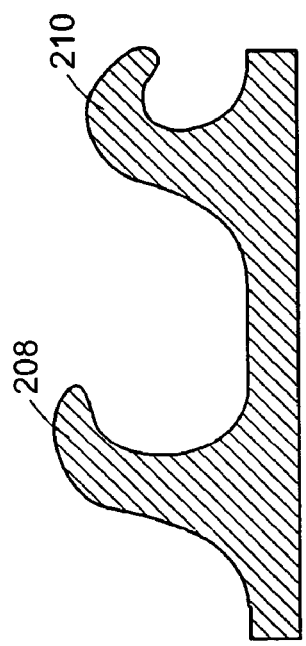
FIG. 4E are side views of other alternative hook shapes.

FIG. 4B illustrates another suitable alternative process for forming the sheet-form fastener shown in FIG. 1 and FIG. 2. In this process, the extruder 200 injects molten plastic directly onto a rotating mold roll 202. Multiple lanes of plastic exiting the die produce multiple lanes in the fastener product (not shown). The fastener elements extending outwardly from the sheet-form base can initially be in the form of a lightly crooked hook 208 or a stem 212, as shown in FIG. 4C and FIG. 4D, respectively. After the sheet-form base is stripped from mold roll 202, the shape of the engaging fastener elements may be modified with roll 206, to form a sharply crooked hook 210 or a disk shaped head 214, as shown in FIG. 4C and FIG. 4D, respectively. FIG. 4E illustrates other possible engaging fastener element shapes.

We define different polymeric materials to mean polymeric materials of different chemical composition or polymeric materials of nearly the same chemical composition, but with different physical properties. Differing physical properties may arise, for example, from differing polymer chain lengths, differing distribution of chain lengths, microstructure of the polymer, additives, etc. Thus, different polymeric materials not only include polypropylene and a polypropylene-based thermoplastic elastomer vulcanizate (e.g., SANTOPRENE® elastomer), but also two different melt flow grades of polypropylene.

Adhesion of the alternating lanes 14 and 16 may become an issue if the materials that make up lanes 14 and 16 do not adhere well to each other. In this case, compatibility agents may be added to the first polymeric material, the second polymeric material or to both the first and second polymeric materials. Compatibility agents can increase the bond strength of the side-by-side lanes and, as a result, can prevent the lanes from separating. For example, a lane of nylon-12 can be made more compatible with a lane of a styrenic elastomer copolymer by adding approximately 10% of a polyether-based polyurethane elastomer to the styrenic elastomer copolymer.

Figure 5:
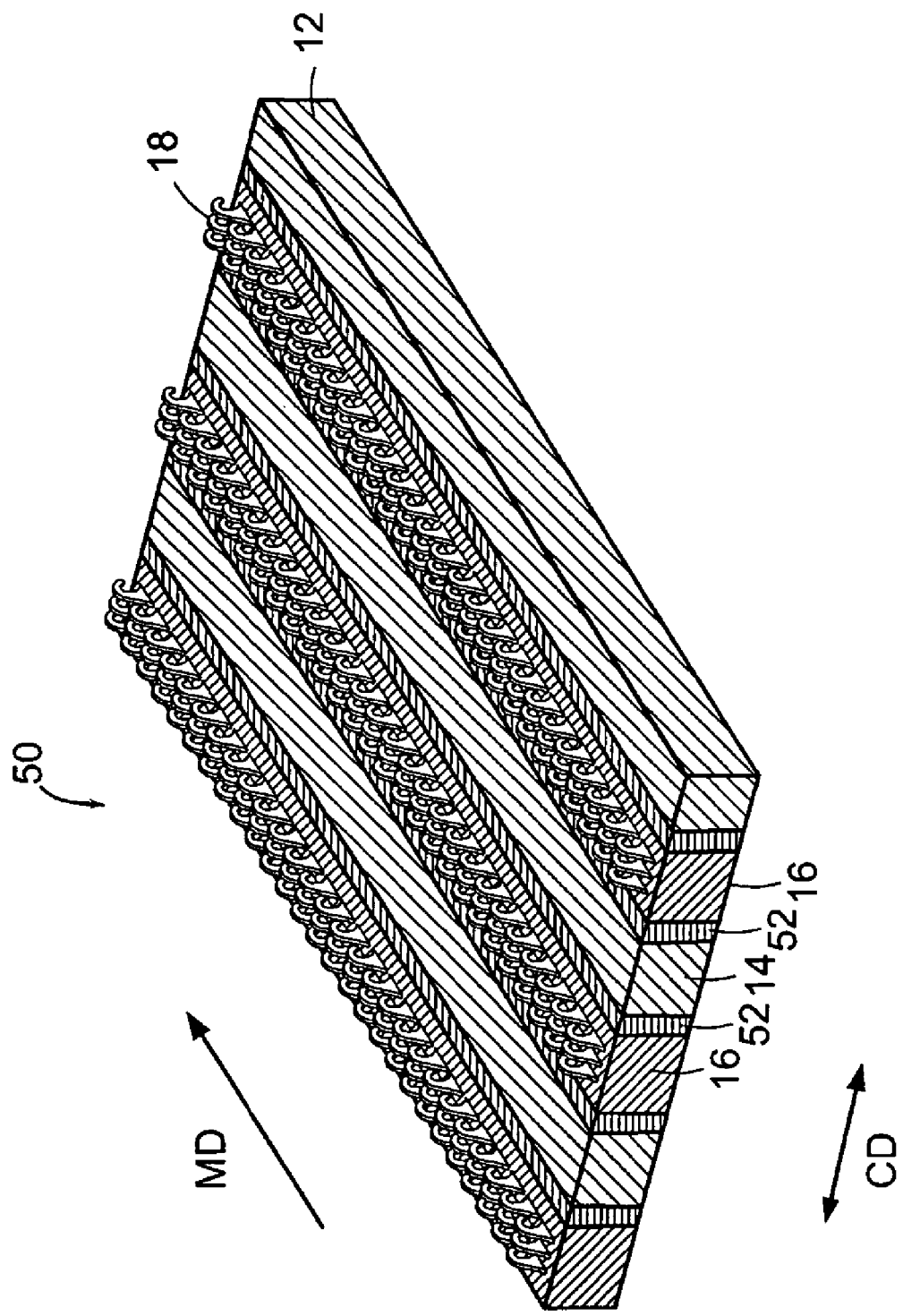
FIG. 5 is a perspective view of an alternative embodiment, illustrating a tie layer.

FIG. 5 shows an alternative embodiment in which a tie layer is provided to bond lanes 14 and 16. Sheet-form fastener 50 includes a plurality of coextruded, side-by-side lanes 14 and 16 extending longitudinally in the machine direction. A tie layer 52 is interposed between lanes 14 and 16. The polymeric material in tie layer 52 bonds well to both of the lanes 14 and 16 and, thus, "bridges" lanes 14 and 16. For example, the tie layer can be a functionalized polyolefin (e.g., maleic anhydride functionalized polyolefin). The width of tie layer 52 in the cross-machine direction (CD) is, for example, from about 0.0005 to about 0.005 inch (about 0.013 mm to about 0.13 mm) or more.

Figure 6:
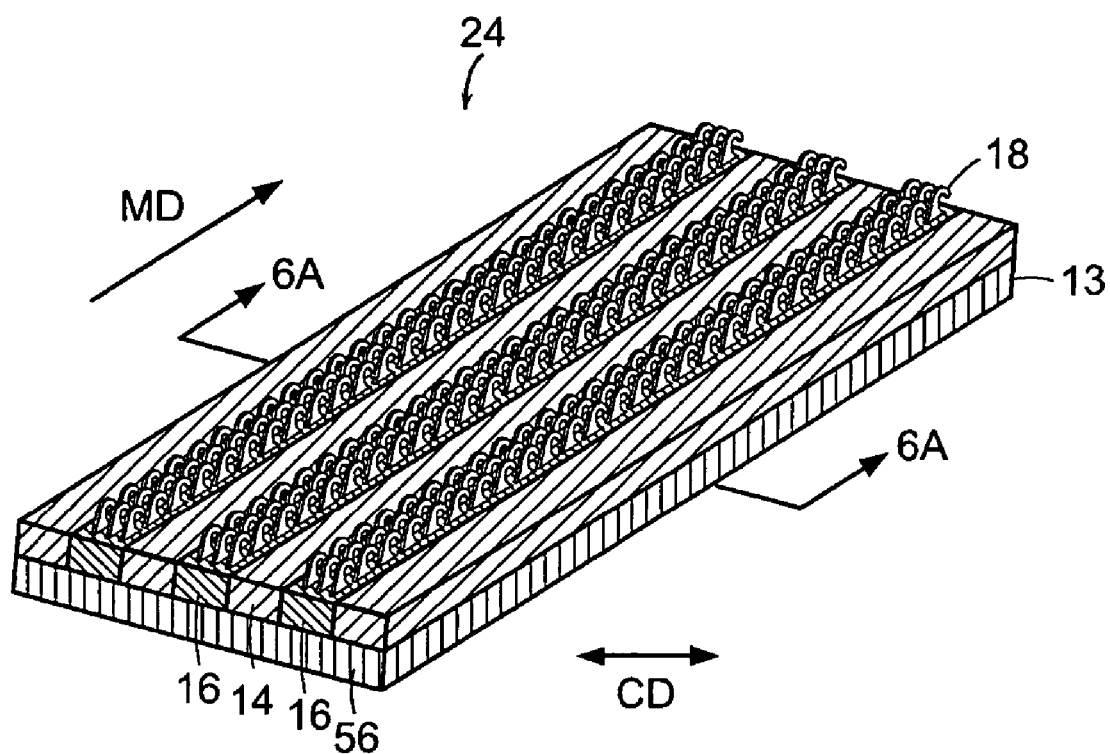
FIG. 6 is a perspective view of an alternative embodiment, illustrating an adjoining layer.
Figure 6A:
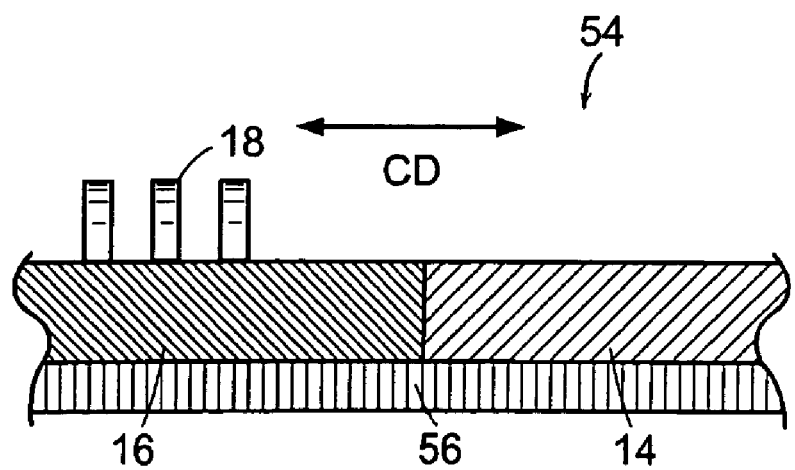
FIG. 6A is an enlarged cross-sectional view of a portion of the embodiment shown in FIG. 6, taken along line 6A—6A.

FIG. 6 shows another embodiment in which a base layer is provided to bond lanes 14 and 16. The base layer can be woven, non-woven, foam or films. Fastener 54 includes a plurality of coextruded, side-by-side lanes 14 and 16 extending longitudinally in the machine direction. Lanes 14 and 16 are adjoined by a base layer 56 of polymeric material extending longitudinally in the machine direction under lanes 14 and 16, forming the sheet-form base 13. U.S. Pat. 5,518,795 and 5,744,080, the entire contents of which are incorporated by reference herein, describes the preparation of laminate hook fasteners having a similar base layer. FIG. 6A shows an enlarged cross-sectional view. The polymeric material in base layer 56 bonds well to both of the lanes 14 and 16. The thickness of base layer 56 is, for example, from about 0.00001 to about 0.100 inch (about 0.00025 to about 2.5 mm) or more.

Figure 7:
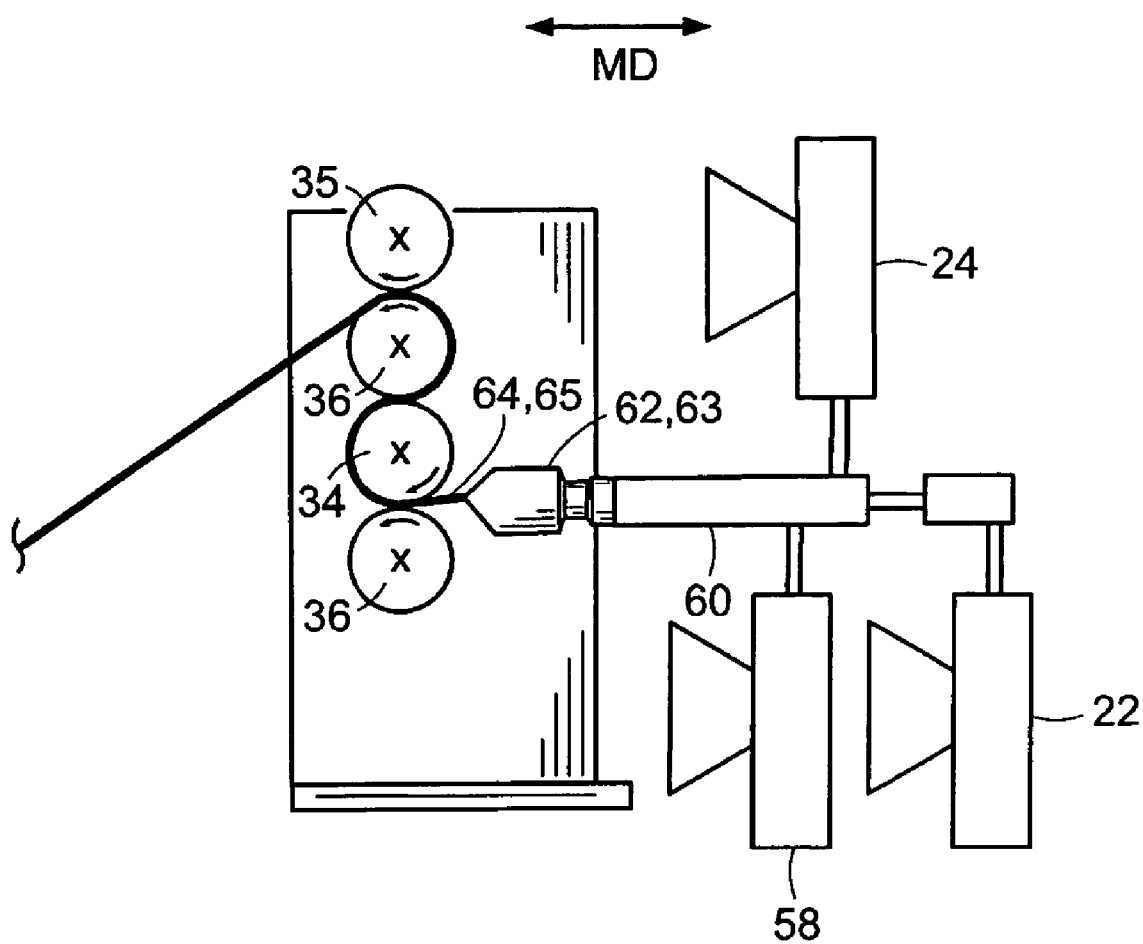
FIG. 7 is a diagrammatic view of a process for making a fastener according to one embodiment.

FIG. 7 illustrates a suitable process for forming the fastener shown in FIG. 5. This process is similar to the process shown in FIG. 4, except, in addition to the extruders 22 and 24, the process utilizes a third extruder 58. Extruder 58 pumps the material of tie layer 52 through stream connecter 60. All material streams come together at die splitter 62, creating a web 64, including tie layer 52 and alternating lanes 14 and 16. The web 64 is pulled through the nip between roll 30 and hook-forming roll 34, forming hooks extending from the web (not shown), and is stripped from 34 by passing the web 64 between stripping rolls 35 and 36. Additional post-processing techniques may be applied to the product exiting the stripping rolls 35 and 36.

FIG. 7 also illustrates a suitable process for forming the product shown in FIG. 6. The setup for this process is similar to that process shown in FIG. 4, except, in addition to the extruders 22 and 24, the process utilizes a third extruder 58. In this case, extruder 58 pumps base layer 56 through stream connecter 60. All material streams come together at die splitter 63, creating web 65, including under base layer 56 and alternating lanes 14 and 16. The web 65 is pulled through the nip between roll 30 and hook-forming roll 34, forming hooks extending from the web (not shown), and is stripped from 34 by passing the web 65 between stripping rolls 35 and 36.

Figure 1A:
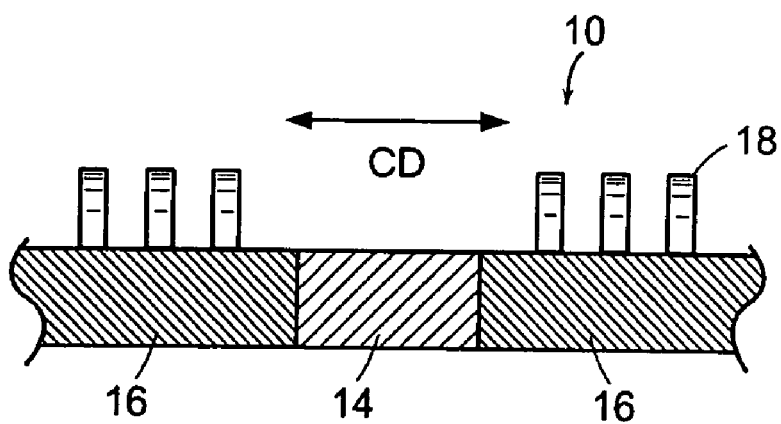
FIG. 1A is an enlarged cross-sectional view of a portion of the fastener shown in FIG. 1, taken along line 1A—1A.

FIG. 8 is a cross-sectional view of a portion of the sheet-form fastener 10 shown in FIG. 1A, with a cut line 8A—8A, indicating where the fastener 10 would be slit to form multiple fasteners. The polymeric material that forms lanes 14 is a softer material than the polymeric material that forms lanes 16, and thus the edges of the fastener tapes will be soft and skin-friendly. FIG. 8A and FIG. 8B show soft-edge sheet-form fasteners 68 and 69 that are derived from sheet-form fastener 10 by cutting along line 8A—8A. FIG. 8C shows a prior art sheet-form fastener 72, with a relatively hard edge as detected by the human finger 70. The cut shown by line 8A—8A can be made by a variety of means known in the art. Examples include, but are not limited to, die cutting, laser cutting, knife cutting, ultra-sonic cutting, air knife, water knife, split line formed by polymers having low adhesion and built-in, perforated split lines. FIG. 8D shows a top view of a diaper tab 74, cut in a non-linear fashion along a lane 14 of the relatively soft polymeric material, exposing a soft edge. Lanes 16 of the diaper tab 74 do not need to have the same type of hook on each lane. For example, "aggressive" hooks may be used in the lanes near the outer edge 75 of the diaper tab to create a product with high shear performance and high peel strength, while maintaining a soft edge. When lanes 14 are made of a thermoplastic elastomer, the improved stretch in the cross-machine direction can make diaper tab 74 engage better with complementary loop material (not shown) and can make it less likely to be inadvertently removed. A suitable polymeric material is a thermoplastic elastomer vulcanizate (e.g., SANTOPRENE® elastomer). The hardness of lanes 14 may be, for example, from about 45 shore A to about 75 shore D. To make material more sticky, tackifying agents may be used.

Figure 8E:
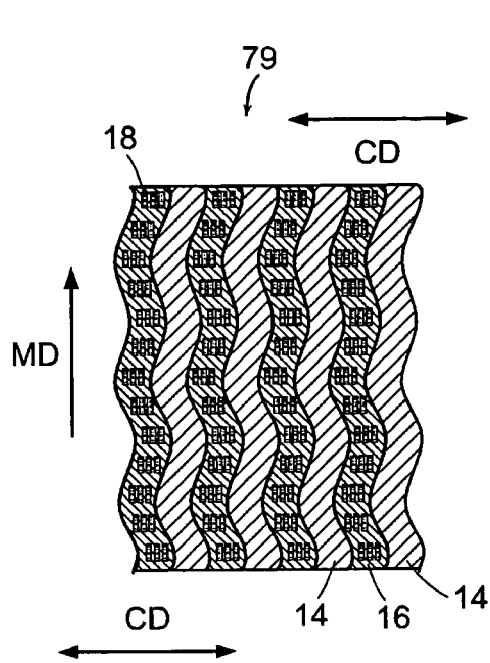
FIG. 8E shows a top view of fastener having non-linear lanes.

FIG. 8E shows a top view of a portion of a diaper tab 79, with non-linear, alternating lanes. Lanes 14 are formed from a relatively soft material and lanes 16 are formed from a relatively hard material. The sheet-form fastener shown in FIG. 8E can be made by the process shown in FIG. 3A, using traversing dies. Preparing a diaper tab in this manner creates a soft-edge fastener and can eliminate the need for cutting in the machine direction (MD).

Figure 8F:
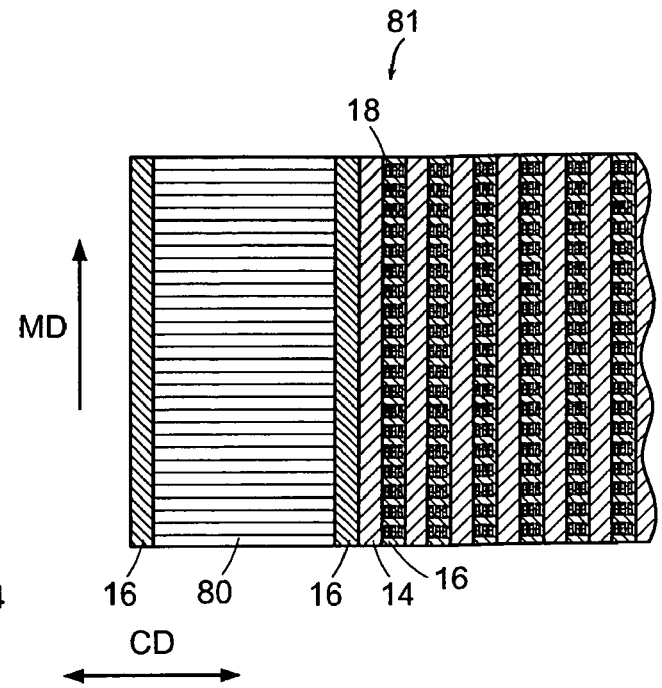
FIG. 8F shows a top view of a fastener having lanes of different widths and functions.
Figure 8G:
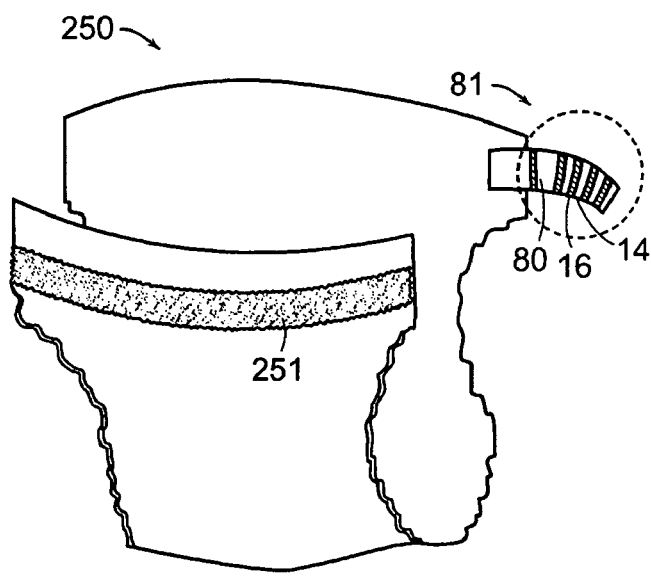
FIG. 8G is a perspective view of a diaper including the fastener of FIG. 8F.

FIG. 8F shows a top view of a diaper tab 81, cut in a non-linear fashion along lane 14 of a relatively soft, tacky polymeric material, exposing a soft-edge. In addition, this tab 81 has a wider lane 80 of the relatively tacky, soft material, disposed between two lanes 16, each without hooks. This wider lane 80 can, for example, add additional stretch for better engagement. Wide lane 80 can come into contact with the skin of a baby and can act as an additional anchoring point. FIG. 8G shows diaper tab 81 attached to diaper 250. Diaper tab 81 is fastened to complementary loop material 251 to close the diaper 250.

FIG. 9 shows yet another embodiment. In this embodiment, sheet-form fastener 76 includes a sheet-form base 12, formed from alternating lanes 14 and 16. The polymeric material that forms lanes 14 is softer than the polymeric material that forms lanes 16. Fastener hooks 18 extend outwardly from the harder polymeric material lanes 16. Suitable materials for lanes 14 may include thermoplastic elastomers (e.g., SANTOPRENE® elastomer). In addition to the lanes 14 being formed from a softer material than the lanes 16, the lanes 14 and 16 are height-differentiated, i.e., lanes 14 have height H1 that is greater than height H2 of lanes 16. Generally, height-differentiation can help "shroud" or hide the hooks 18. Height differences in the fastener product can be created by making the appropriate complementary mold roll 34. FIG. 9A shows a cross-sectional view of the sheet-form fastener 76 shown in FIG. 9. Cutting the fastener along line 9B-9B results in height-differentiated, soft-edge fasteners 77 and 78, shown in FIG. 9B and FIG. 9C, respectively. Height-differentiation provides, for example, additional protection of the user's skin against the relatively hard hooks 18 extending outwardly from lanes 16. Thus, a human finger moving gently across the sheet-form fastener 76 in the cross-machine (CD) direction will be more likely to contact the soft material of lanes 14, rather than the relatively hard hooks 18. Of course, a few hooks may extend above the height of the soft lanes 14 without significantly reducing the softness and safety of the overall product. Lanes 14 of the relatively soft material may also include hooks (not shown), providing additional height-differentiation and, therefore, additional "soft-touch" and safety. The height-differentiation should not be so large that the hooks 18 cannot engage loops of a female fastener component (not shown) to form a complete hook and loop fastener.

Figure 10:
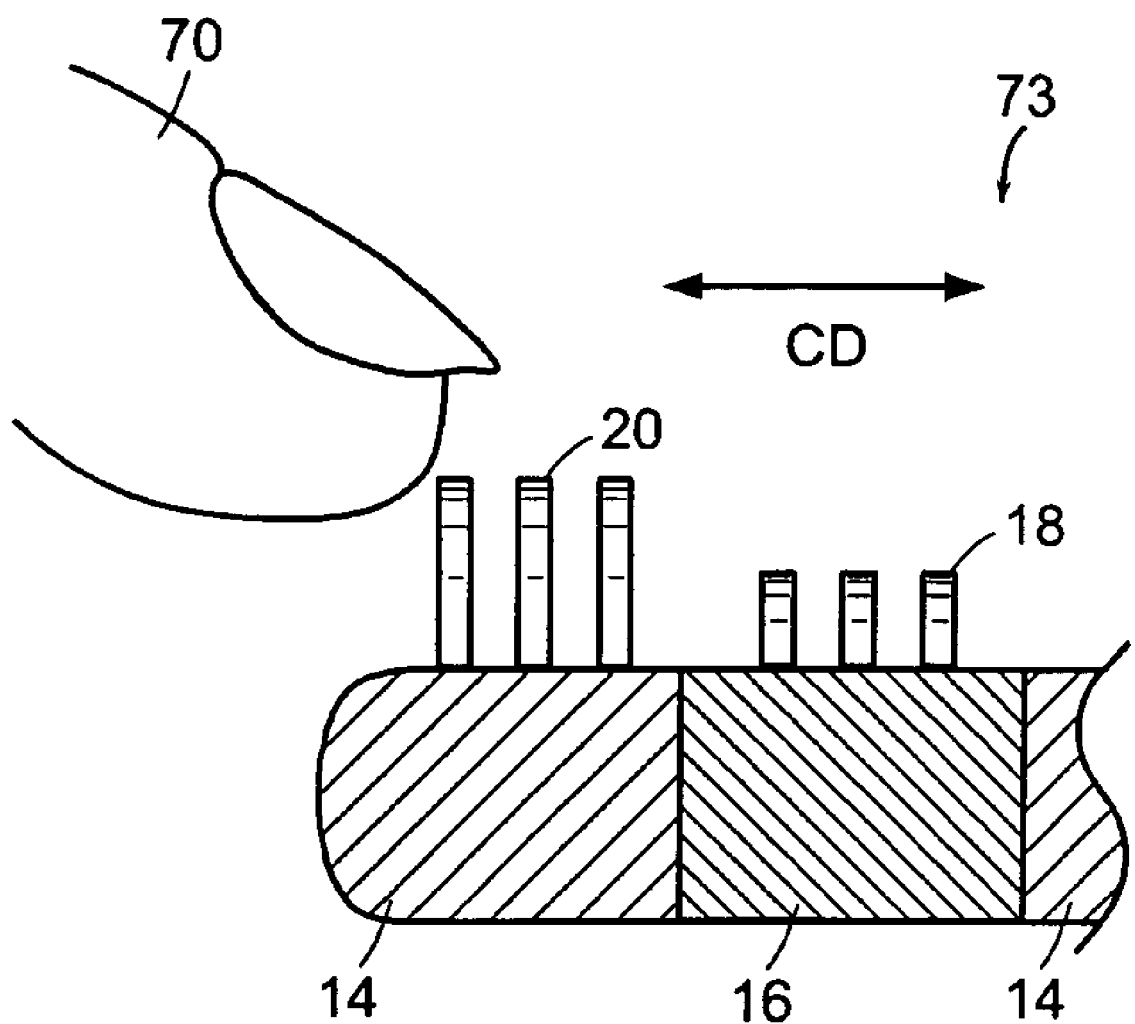
FIG. 10 shows an enlarged view of another fastener including height-differentiation.

FIG. 10 shows a fastener 73 that features lanes 16 of a relatively hard material with hooks 18 extending outwardly and lanes 14 of a relatively soft material with hooks 20 extending outwardly. The hooks 18 and 20 are height-differentiated, i.e., the distal ends of the hooks 20 extending outwardly from the lanes formed of the softer material 14 are generally higher than most of the distal ends of the hooks extending outwardly from lanes 16. A human finger 70 moving gently across such a sheet-form fastener in the cross-machine (CD) direction will be more likely to contact the soft hooks 20 extending outwardly from lanes 14, rather than the shorter, relatively hard hooks extending outwardly from lanes 16. This embodiment provides additional skin-friendliness and safety. The softer hooks 20 may or may not serve the purpose of engaging a corresponding female loop component. For example, the hooks 20 may be replaced by non-engagable stems (not shown). It is generally important that the height-differentiation not be so large that the soft hooks 20 prevent the harder hooks 18 from engaging the loops of a female component (not shown) to form a complete hook and loop fastener.

Figure 11A:
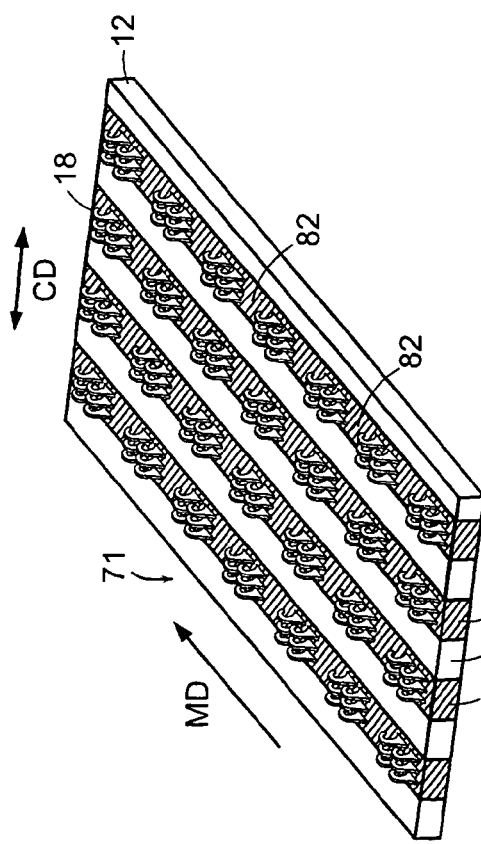
FIG. 11A shows a perspective view of a fastener including discontinuously molded hooks.

FIG. 11A shows a perspective view of a sheet-form fastener 71 having hooks 18 that are discontinuously molded on lanes 16. By discontinuously, we mean that there are relatively large regions 82 where hooks are absent. Regions of discontinuity may, for example, improve safety by reducing the number of relatively hard hooks. The length of the regions of discontinuity 82, as measured longitudinally in the machine direction (MD) may be, for example, from about 0.005 to about 10 inches (about 0.13 mm to about 254 mm), depending upon the application.

Figure 11B:
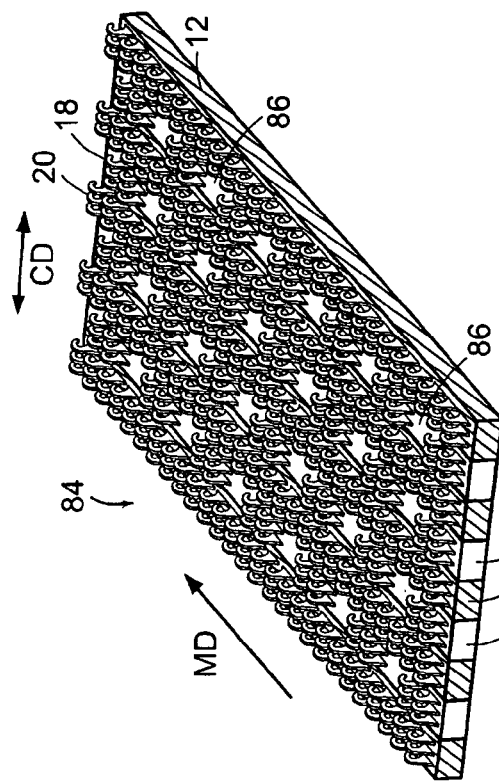
FIG. 11B shows a perspective view of another fastener including discontinuously molded hooks.

FIG. 11B shows a perspective view of a sheet-form fastener 84 similar to that shown in is FIG. 11A, but with hooks 20 extending from lanes 14. Hooks 20 may be discontinuously molded on lanes 14 (not shown).

Figure 11C:
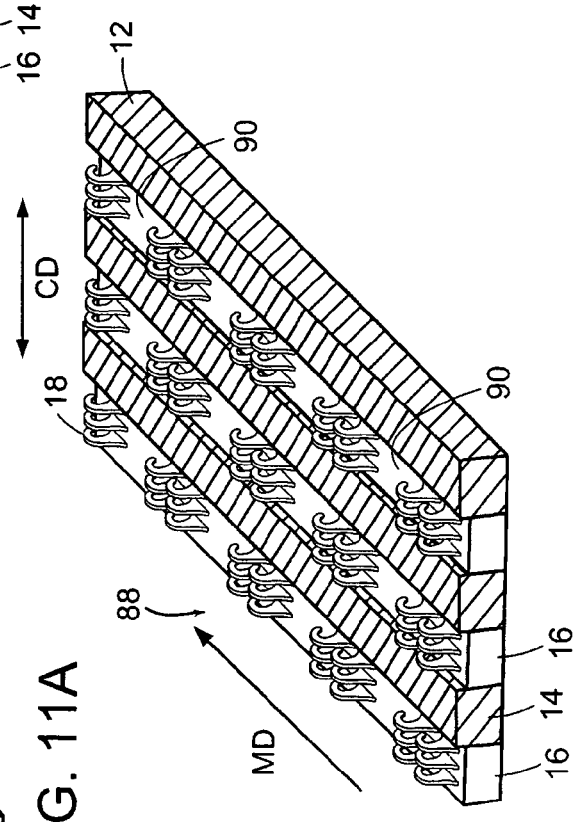
FIG. 11C shows a perspective view of another fastener including discontinuously molded hooks.

FIG. 11C shows a perspective view of a sheet-form fastener 88 in which lanes 14 and lanes 16 are height-differentiated and the hooks 18 are discontinuously molded on lanes 16.

Figure 12:
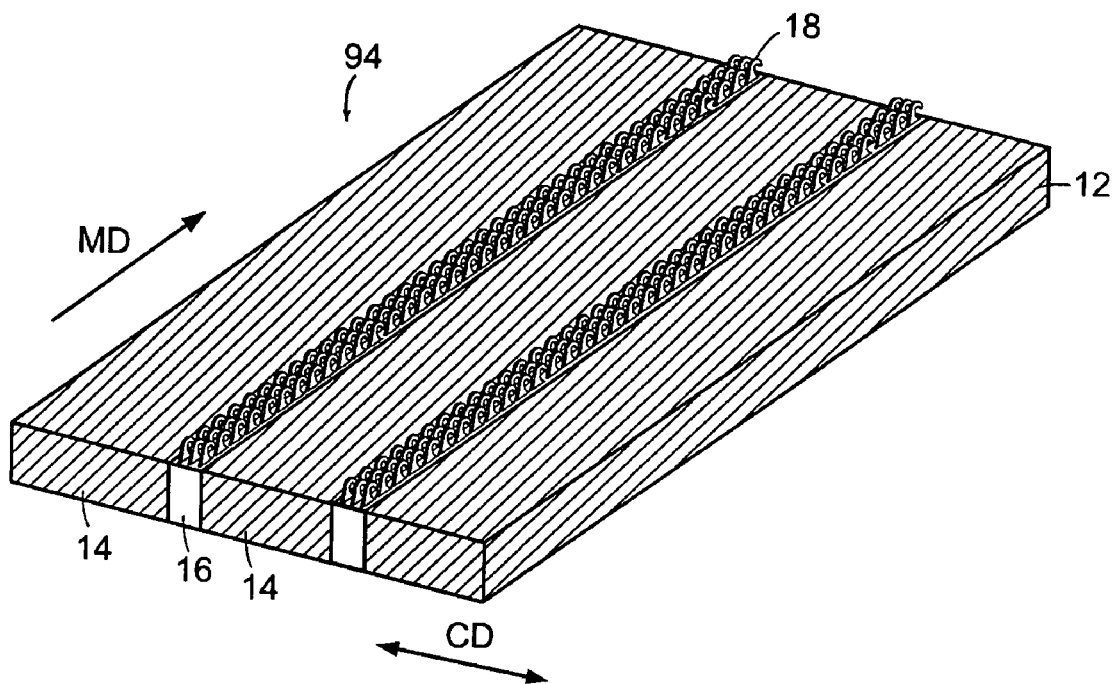
FIG. 12 shows a perspective view of another fastener including different width lanes.

FIG. 12 shows a fastener 94 having a greater degree of stretch as a result of increasing the width of relatively soft lanes 14 relative to the width of lanes 16. A greater degree of stretch may, for example, increase engagement of the hooks with a loop material (not shown) and may, for example, increase safety and skin-friendliness. The softer the material used for lanes 14, the greater the degree of stretch imparted to fastener 94.

Figure 13:
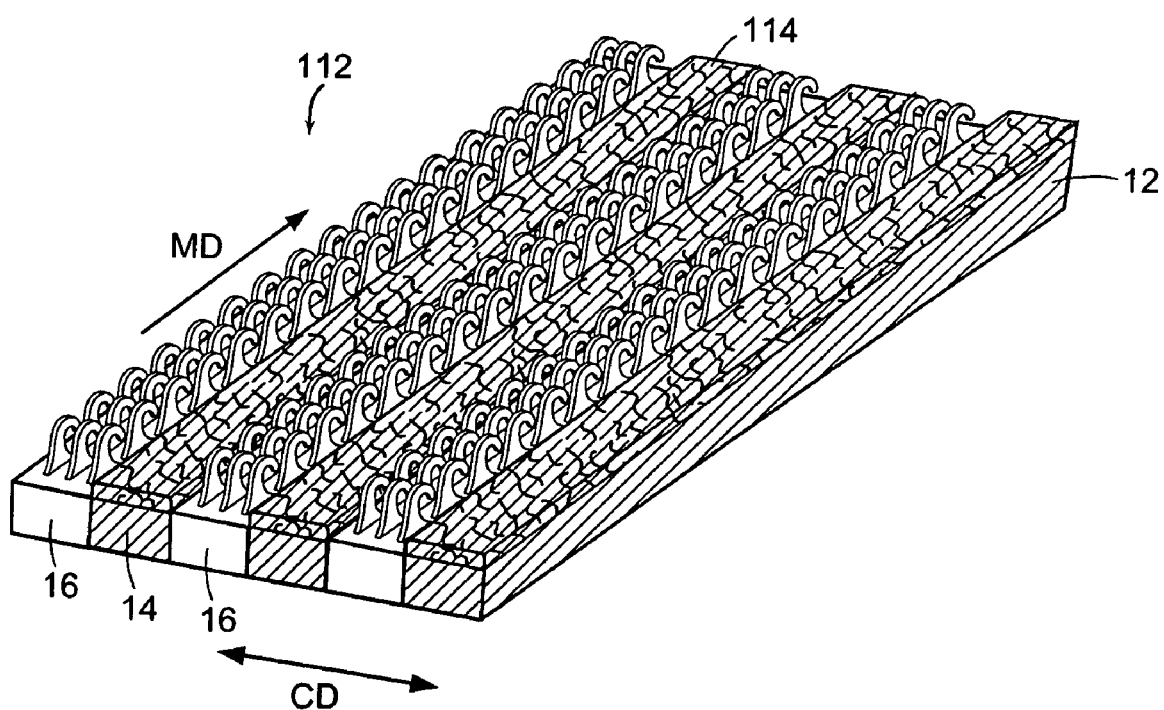
FIG. 13 is a perspective view of a fastener with fiber added.

FIG. 13 shows a sheet-form fastener 112 in which the polymeric material that forms lanes 14 is a softer and tackier material than the polymeric material that forms lanes 16, and a fiber 114 is adhered to the tacky lanes 14. Bonding can be, for example, the result of the inherent tackiness of the lane 14 or can be achieved or enhanced by, for example, the addition of other resinous materials such as curable adhesive. If additional resinous material is used to bond the fiber to the fastener, the resinous material may be cured using UV light, heat or other techniques. The fiber 114 cause the lanes to be height-differentiated resulting in a skin-friendly soft touch fastener product. The fiber can be cotton or fine denier polypropylene. The bonding agents may be, for example, acrylic or polyurethane.

Figure 14A:
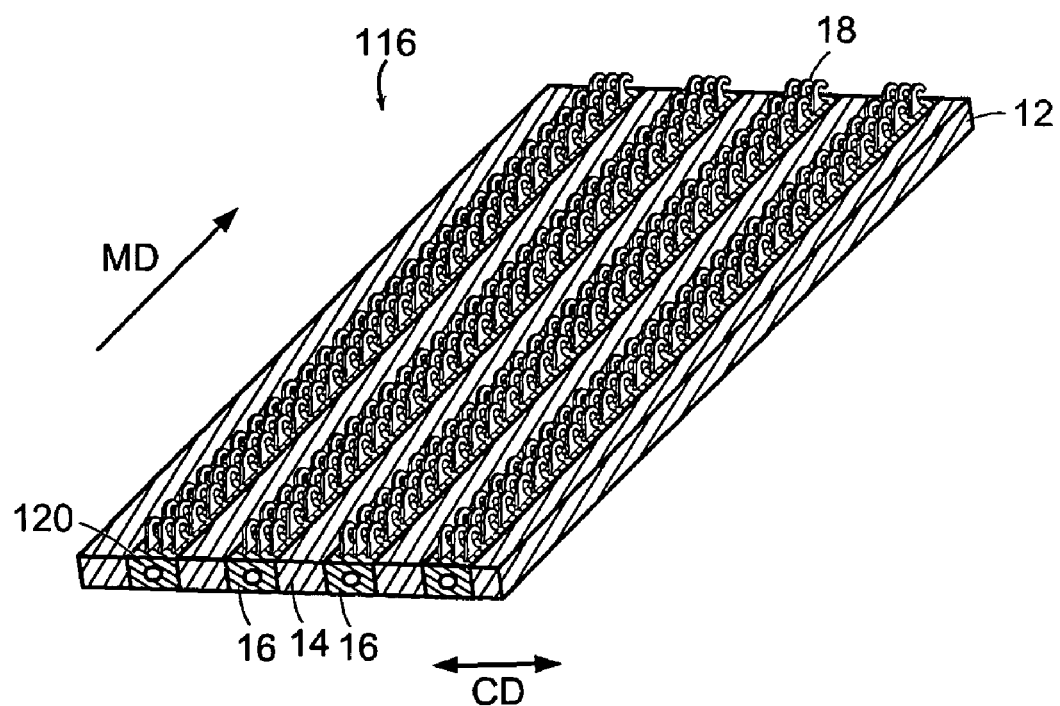
FIG. 14A is a perspective view of a fastener including longitudinal cavities.
Figure 14B:
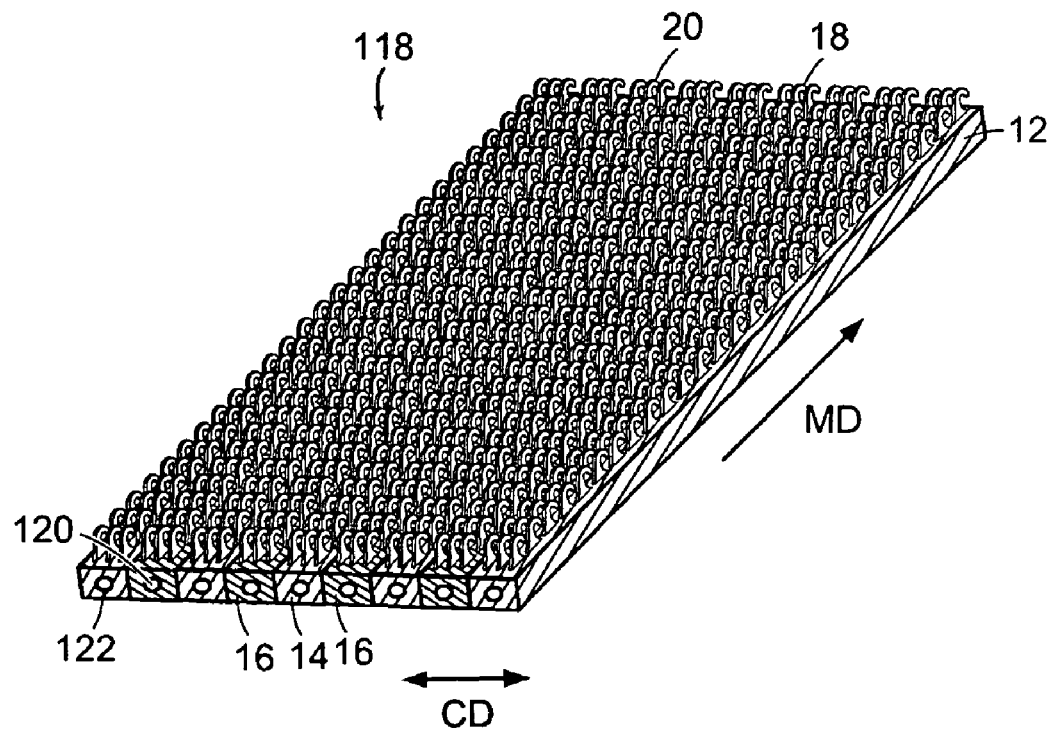
FIG. 14B is a perspective view of another fastener including longitudinal cavities.

FIG. 14A shows a sheet-form fastener 116 having cavities 120 that extend longitudinally through lanes 16. The cavities may be un-filled (hollow) or they may be filled with a material. Similarly, FIG. 14B shows a sheet-form fastener 118 with cavities 120 and 122 that extend longitudinally through lanes 14 and 16, respectively. Some longitudinal cavities may be filled, while some longitudinal cavities may be un-filled. If the longitudinal cavities are filled, fillers may include, for example, shape memory polymers. For example, the shape memory polymer may be DIAPLEX® polyurethane shape memory polymer. The cavities may also be filled with, for example, metal wire for bendability and rigidity, electrical conductors and optical fibers.

Figure 14C:
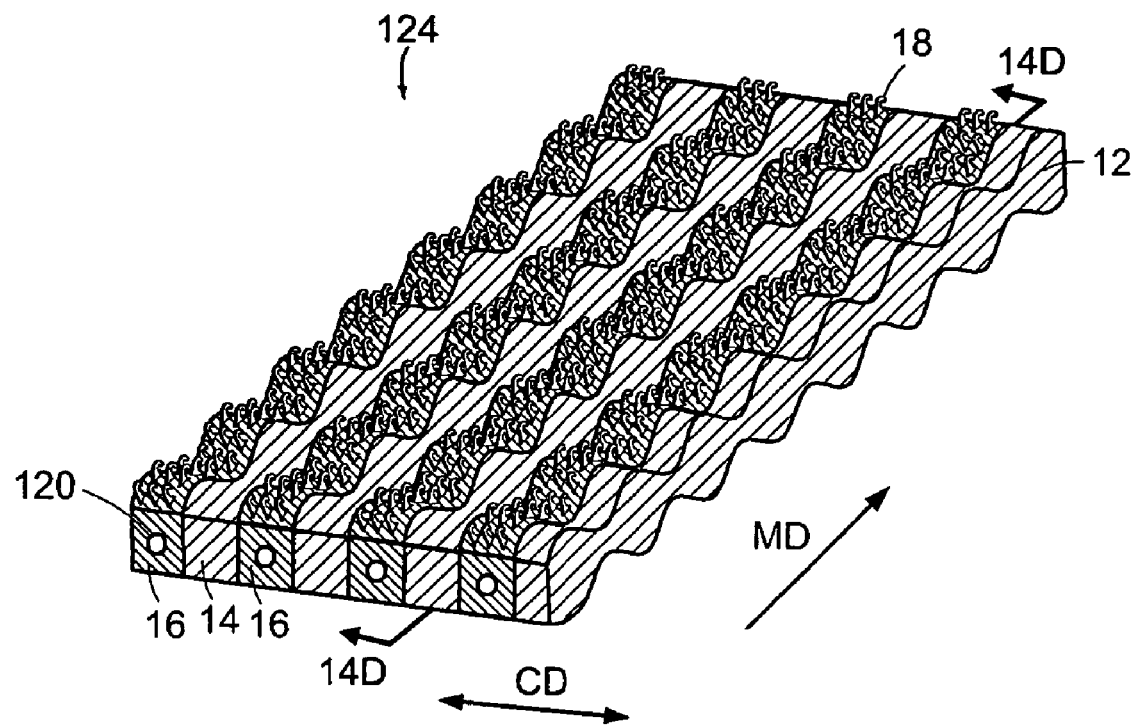
FIG. 14C shows a perspective view the fastener shown in FIG. 14A after stretching in the machine direction.
Figure 14D:
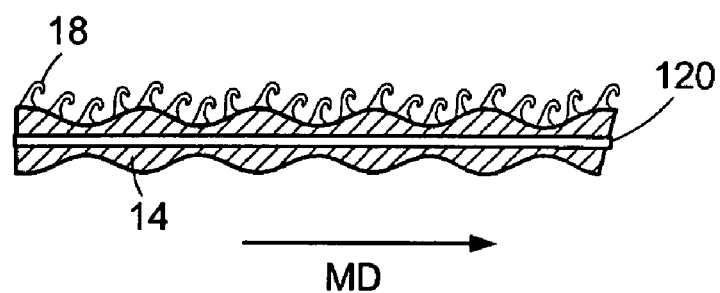
FIG. 14D shows a cross-sectional view of the fastener shown in FIG. 14C, taken along line 14D—14D.

FIG. 14C shows a sheet-form fastener 124, resulting from post stretching after forming hooks 18 in the machine direction. Various structures with different three-dimensional shapes are possible, depending upon the materials used for lanes 14 and 16 and depending upon the material used (if any) for filling the longitudinal cavities 120. Such a structure can allow for a more skin-friendly hook fastener because many of the hooks are "shrouded" in the three dimensional, rippled structure of the stretched hook fastener. Simply pushing the structure flat exposes more hooks to engage the loops of a loop component (not shown). FIG. 14D shows a cross-sectional view taken in the machine direction, along line 14D—14D of FIG. 14C. Hooks 18 form complex angles due to the rippled shape of the underlying structure. These complex angles can allow for, for example, better engagement, better shear strength, improved safety and "soft touch."

Figure 15A:
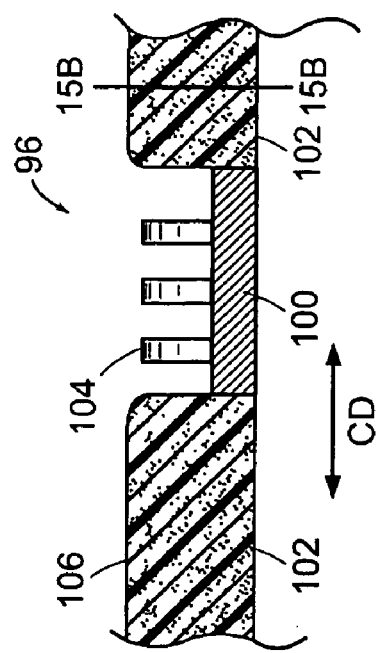
FIG. 15A is an enlarged cross-sectional view of a portion of the fastener shown in FIG. 15, taken along line 15A—15A.
Figure 15B:
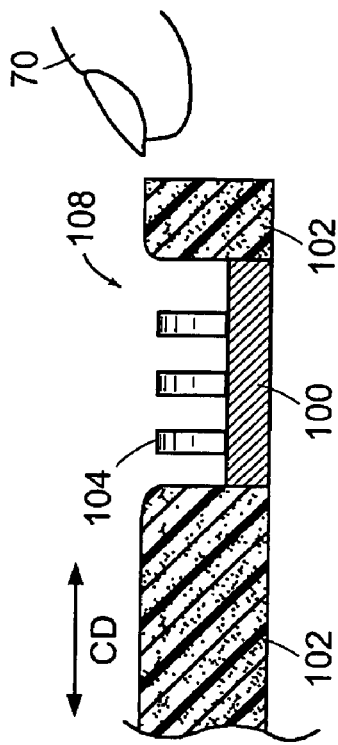
FIG. 15B shows the embodiment illustrated in FIG. 15A, after cutting along line 15B—15B in FIG. 15A.
Figure 15:
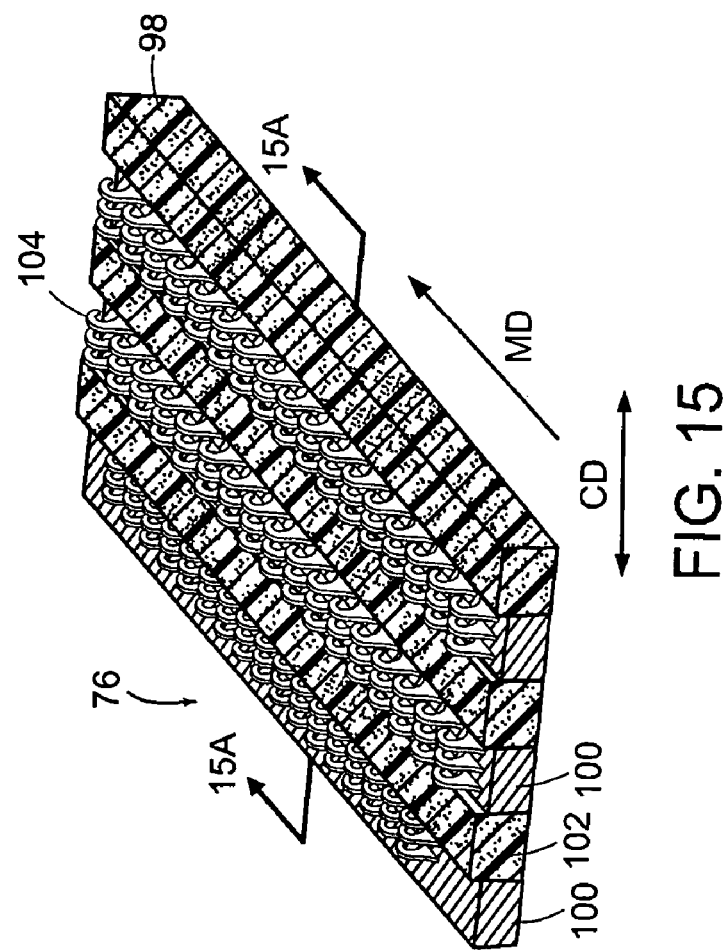
FIG. 15 shows a perspective view of a fastener including foam lanes.

FIG. 15 shows a sheet-form fastener 96, including a plurality of coextruded, alternating, side-by-side lanes extending longitudinally in the machine direction (MD), forming a sheet-form-base 98. The sheet-form base includes a lane 100 of a polymeric material and a lane 102 of polymeric foam. A plurality of molded fastener elements 104 extend outwardly from, and integral with, the lanes 100. Lanes 100 and lanes 102 are height-differentiated, as discussed above. In some instances, lane 100 is made of a thermoplastic polymer and lane 102 is made of a foamed thermoplastic polymer. In other instances, lane 100 is a non-elastomeric thermoplastic polymer, e.g., polypropylene, and lane 102 is made of a foamed elastic polymer, e.g. a polypropylene-based thermoplastic elastomer vulcanizate (e.g., SANTOPRENE® elastomers).

Lane 102 may be foamed by a variety of methods, including using, fo example, a chemical foaming agent (e.g., HYDROCEROL® chemical foaming agent available from Clariant Corporation, Holden, Mass.) or by injecting a gas (e.g., carbon dioxide, nitrogen or others) into the plastic that is to form lane 102. FIG. 15A shows an enlarged cross-sectional view of a portion of the sheet-form fastener 96, taken along line 15A—15A. In this particular case, a height-differentiated fastener is shown, where the height of lane 102, with foam voids 106, is greater than the height of the hooks 104 extending outwardly from lane 100. The fastener shown in FIG. 15A may have lanes of the same height and/or some hooks may be molded in lanes 102. As discussed above, adhesion between lanes 100 and 102 may be optimized by using a tie layer. Also, an adjoining layer may be bonded below lanes 100 and 102 (not shown). FIG. 15B shows a soft edge fastener 108, formed from cutting fastener 96 along line 15B—15B.

Other methods of forming sheet-form fastener 96 may be used. For example, lanes 100 with hooks 104 and lanes 102 may be formed in a separate step and bonded together later in the process. Using this method, lane 102 may be, for example, formed of a foamed thermoset plastic (e.g., polyurethane) instead of a thermoplastic. Likewise, lane 100 may be formed of a thermoset. Thermosets may be advantageous when, for example, the products are used in a harsh environment.

Figure 16:
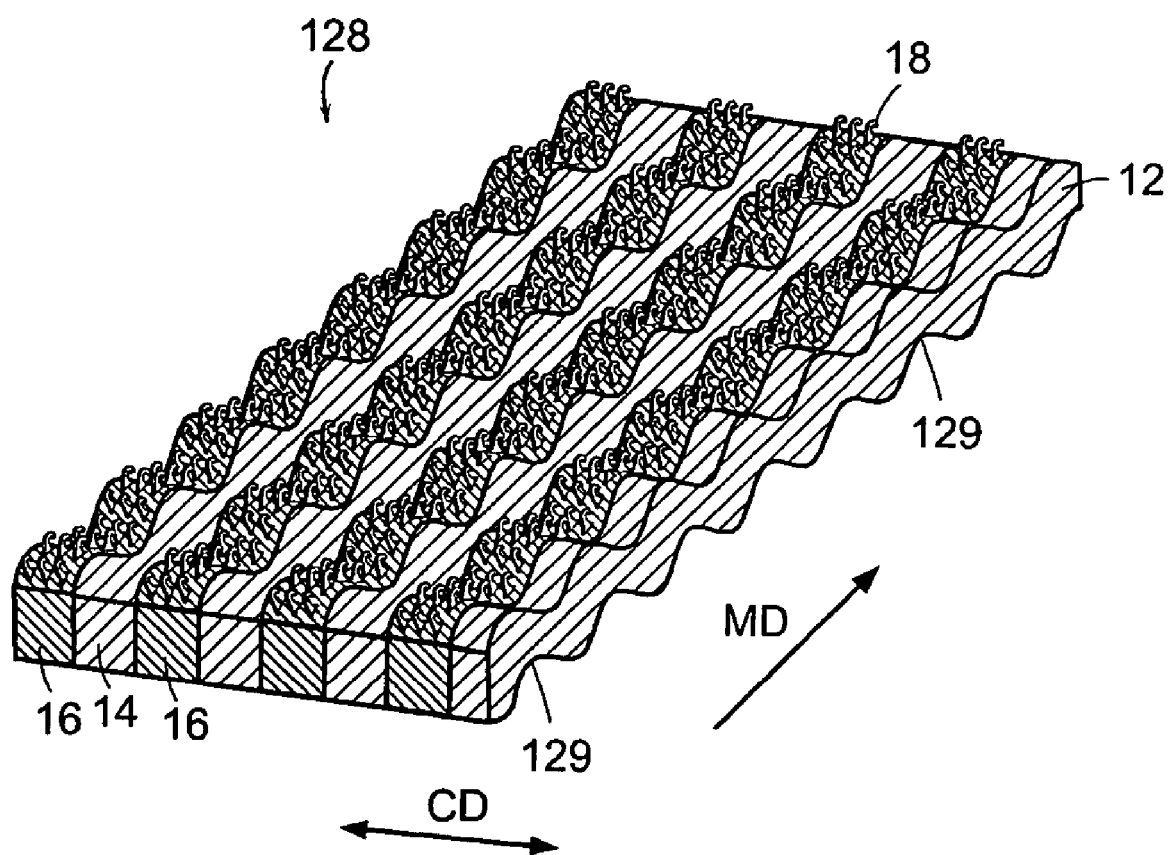
FIG. 16 shows a perspective view of a fastener produced by stretching a fastener similar to the one shown in FIG. 1 in the machine direction.

FIG. 16 shows a sheet-form fastener 128 having a three dimensional, ripple-type structure that can result from stretching fastener 10 shown in FIG. 1 in the machine direction. The three dimensional, ripple-type structure results from the differing physical properties of the materials that make up lanes 14 and 16 and their different tendencies to return to their initial (un-stretched) state. In some instances, the thickness of the sheet-form base changes during stretching in a non-uniform way, resulting in "kinks" 129 in the ripple structure. In other instances, the thickness of the base changes in a more uniform way, resulting in the structure shown in FIG. 16A and discussed below. Such a ripple-type structure may allow for, for example, a more skin-friendly hook fastener because many of the hooks are "shrouded" in the three dimensional, rippled structure of the stretched hook fastener.

Figure 16A:
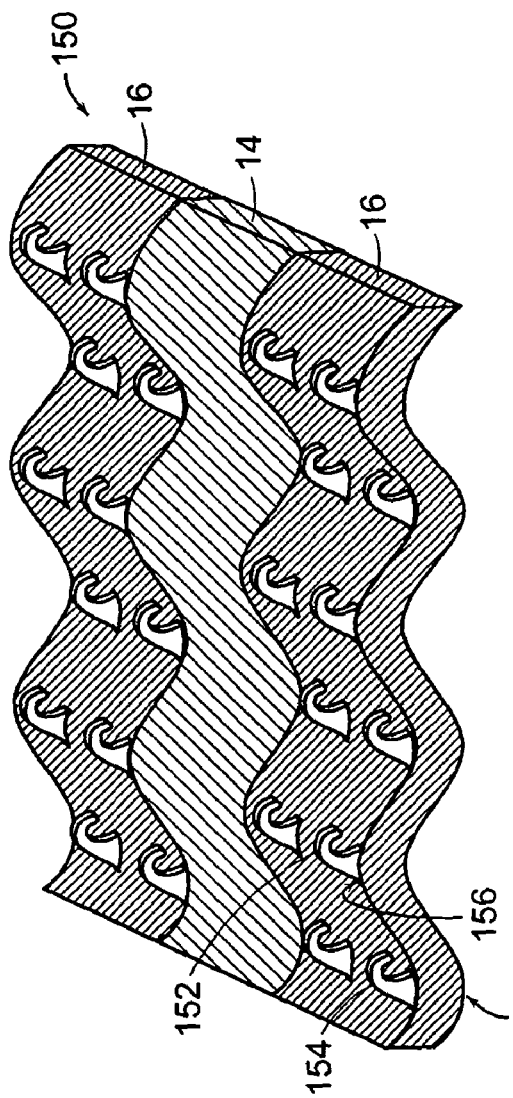
FIG. 16A shows a perspective view of another fastener produced by stretching a fastener similar to the one shown in FIG. 1 in the machine direction.
Figure 16C:
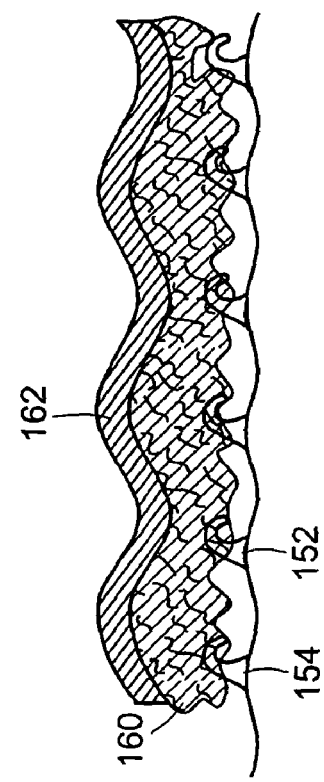
FIG. 16C shows the fastener of FIG. 16A with peak and trough hooks engaging loop material.
Figure 16B:
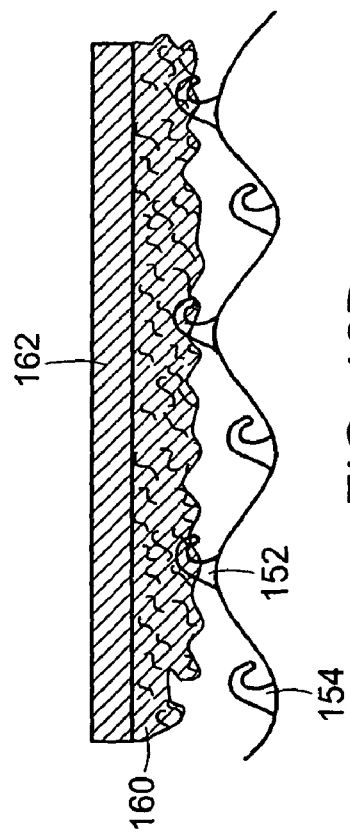
FIG. 16B shows the fastener of FIG. 16A with peak hooks engaging loop material.

FIG. 16A shows a three dimensional, ripple-type fastener 150, with alternating lanes 14 and 16. Hooks 152 extend from peaks 156 in lanes 16, while hooks 154 extend from troughs 158 in lanes 16. This three dimensional, ripple-type structure can result from, for example, stretching fastener 10 shown in FIG. 1 in the machine direction. In this instance, the thickness of the base changed in a uniform way upon stretching. FIG. 16B shows the fastener of FIG. 16A engaging a loop material 160 connected to a support base 162 and illustrates that only hooks 152 on the peaks 156 of the fastener engage the loop material in response to light force. FIG. 16C illustrates that when more force is applied, the hooks 154 in the troughs 158 engage as well. FIC. 16C further illustrates rippling of the loop support structure 162 as a result of the differential forces applied to it by the rippled fastener below.

Figure 16D:
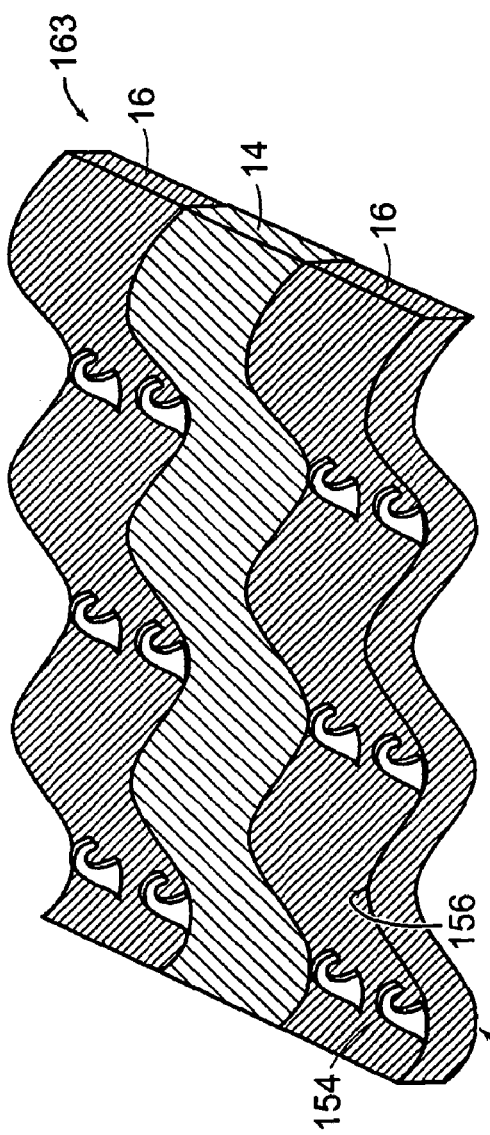
FIG. 16D shows a perspective view of fastener produced by stretching a fastener similar to the one shown in FIG. 1 in the machine direction.
Figure 16F:
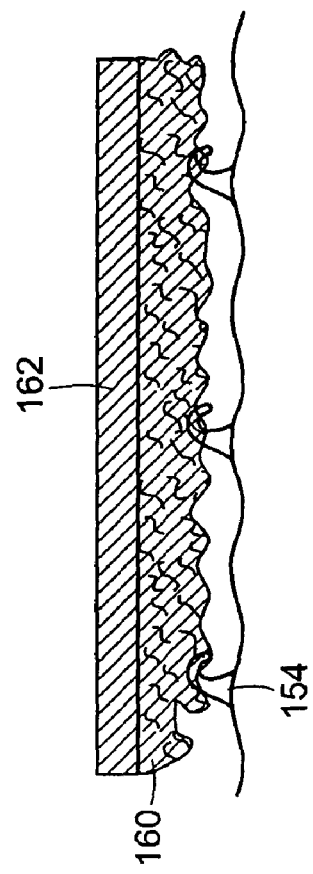
FIG. 16F is a side view that shows the fastener of FIG. 16D with the hooks engaging a loop material.
Figure 16E:
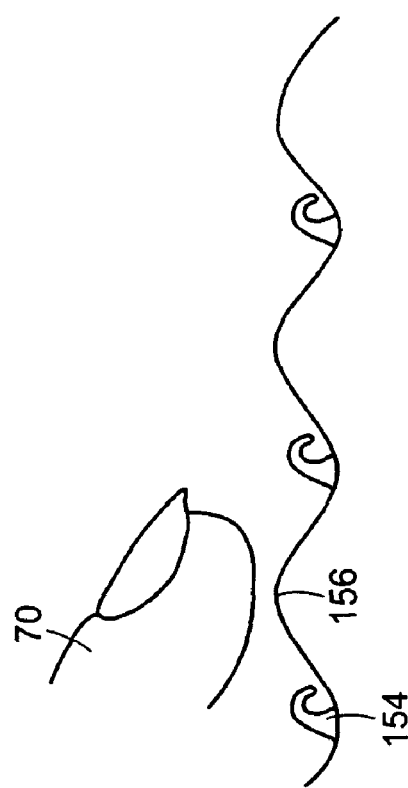
FIG. 16E is a side view of the fastener of FIG. 16D.
Figure 16G:
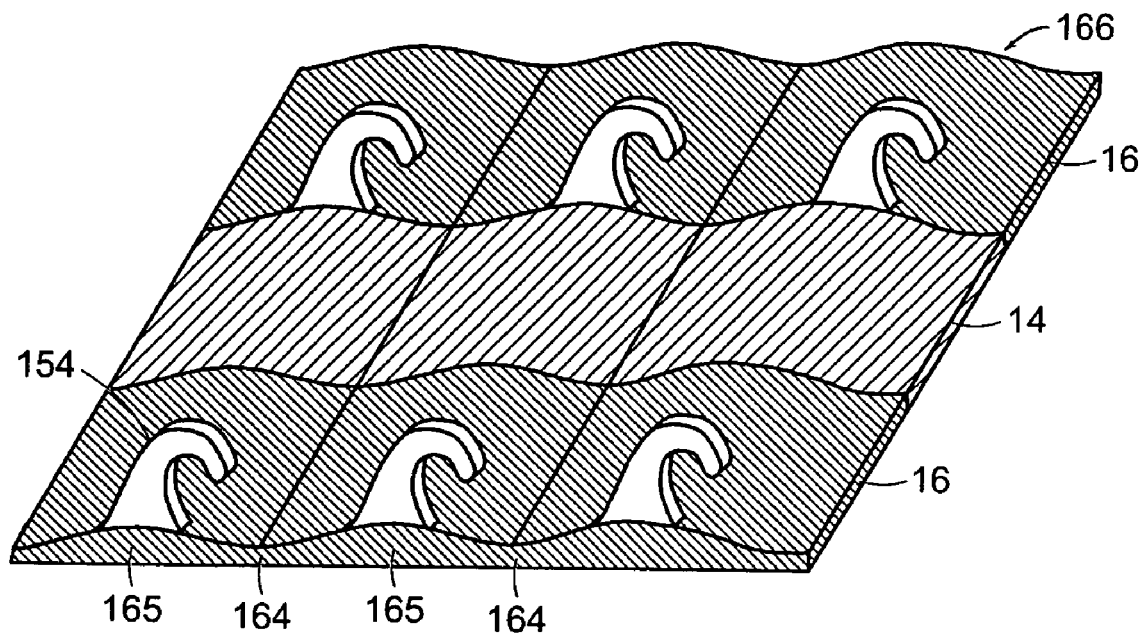
FIG. 16G is a perspective view of a pre-fastener product that upon stretching can generate the fastener of FIG. 16D.

FIG. 16D shows a three-dimensional, ripple-type fastener 163 with hooks 154 only in troughs 158. FIG. 16E illustrates that a hook 154 in a trough 158 is below the level of the peak 156, resulting in a "soft touch" fastener. FIG. 16F illustrates that with force, hooks 154 engage loop material 160 to form a hook and loop fastener. FIG. 16G shows a precursor 166 to the fastener shown in FIG. 16D. This precursor 166 contains thick regions 165 with hooks 154 extending from these regions and thin regions 164 with no hooks. Upon stretching, a fastener similar to the one shown is FIG. 16 or FIG. 16A is produced.

Figure 17:
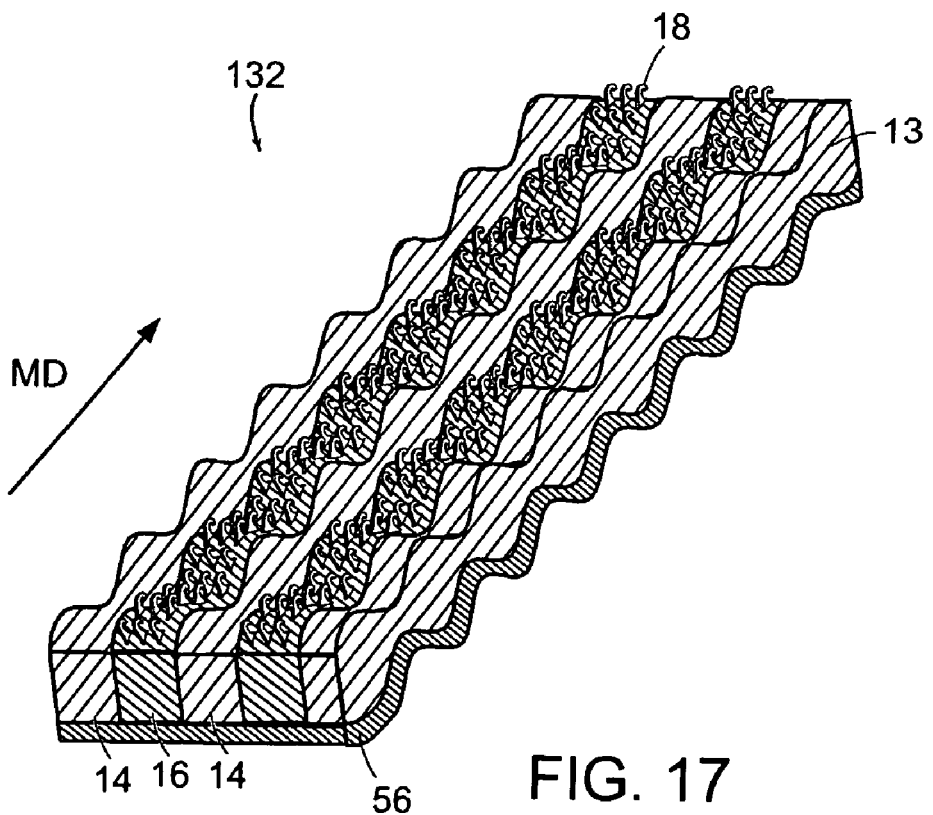
FIG. 17 shows a perspective view a fastener resulting from stretching a fastener similar to the one shown in FIG. 6 in the machine direction.

FIG. 17 shows a possible three dimensional, ripple-type structure 132 resulting from stretching the sheet-form fastener 54 with bottom layer 56 of FIG. 6 in the machine direction.

FIG. 18 shows a sheet-form fastener 139, including lanes 14 and 16 and base layer 56, the base layer 56 being at least extensible. Lanes 16 have molded hooks 18 extending outwardly. Sheet-form fastener 140 shown in FIG. 18A is derived from sheet-form fastener 139 by stretching fastener 139 in, for example, the cross-machine direction (CD). Cross-machine stretching is described by Buzzell, et al. in U.S. Pat. No. 6,035,498, the entire disclosure of which is incorporated by reference. Adhesion between lanes 14 and 16 is relatively poor at the interface 136 between the lanes. Upon stretching, lanes 14 and 16 separate at interface 136, but remain attached to adjoining layer 56. Due to separation, the interface 136 becomes gap 138 (FIG. 18A). In some instances, structure 140 may curl (not shown), forming a three-dimensional structure. Materials for lanes 14 and 16 are chosen to allow the lanes to separate at interface 136 during CD stretching. Thus, generally the two materials are relatively incompatible. Adhesion of lanes 14 and 16 to bottom layer 56 should be good enough so that the lanes of 14 and 16 do not separate from the adjoining layer 56. The structure 140 allows for, for example, greater flexibility of the fastener product, especially in the out of plane directions 141. Greater flexibility allows for, for example, good safety and skin-friendliness. Materials that are normally compatible may be made incompatible by additives. Examples of such additives are TEFLON® fluoropolymer and a relatively high loading of clay (e.g., 25%).

Figure 18B:
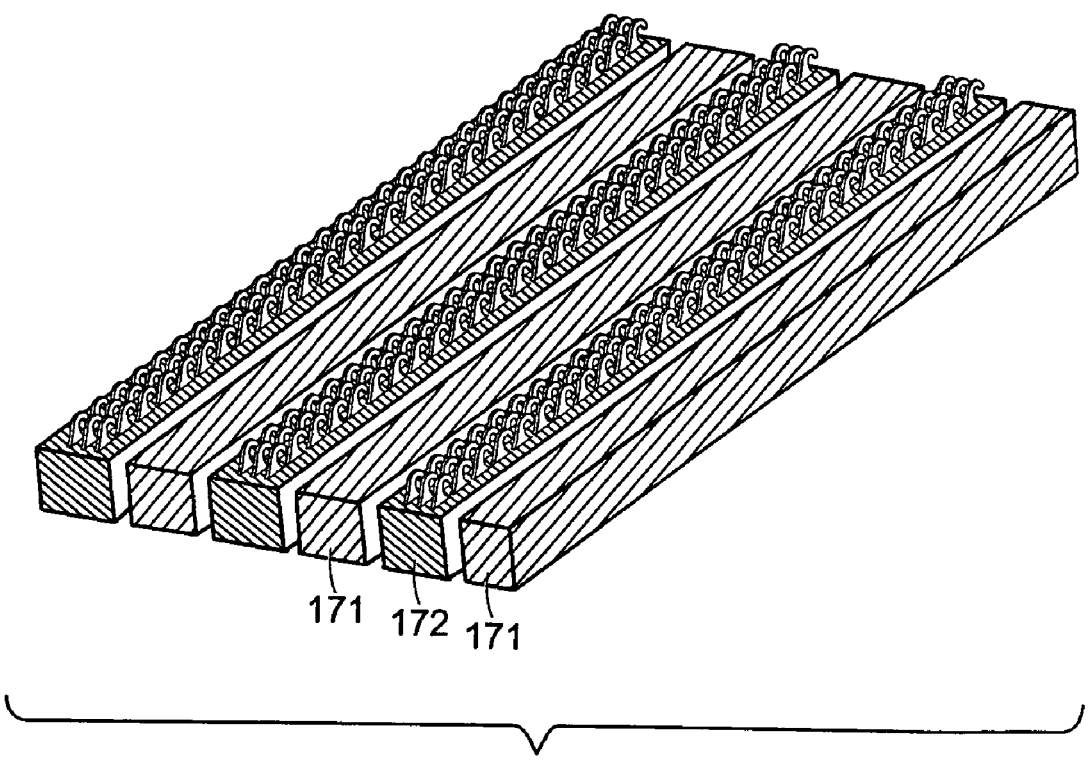
FIG. 18B shows the fastener of FIG. 18A after removal of the adjoining layer.

FIG. 18B shows that removal of the bottom layer 56 from structure 140 yields discrete elements 171 and 172. This could be an efficient method of preparing several different fastener products on one manufacturing line.

FIG. 18C shows a fastener product 176, including, in addition to lanes 14 and 16, lanes 178, 180 and 184. A bottom layer 56 is below the lanes. Upon stretching lanes 14 and 16 separate from one another, but remain attached to the bottom layer 56 (not shown). Upon removal of the bottom layer 56, discrete units 188, lane 14 and 190 result as shown in FIG. 18D.

A number of embodiments of the invention have been described. For example, some of the lanes may be made of a cross-linkable material. Nevertheless, it will be understood that various modifications may be made without departing from the spirit and scope of the invention Accordingly, other embodiments are within the scope of the following claims.

What is claimed is:

1. A method of making a touch fastener, the method comprising:
    forming a plurality of lanes having edges, including a lane comprising a first polymeric material and a lane comprising a second polymeric material which is foamed;
    joining the lanes side-by-side along their edges to provide a composite polymeric sheet; and
    forming a plurality of discrete fastener element stems extending outwardly from at least one exposed surface of the composite sheet.

2. The method of claim 1 further comprising forming engageable heads on the discrete fastener element stems.

3. The method of claim 1 wherein the lanes are joined with an adhesive.

4. The method of claim 1 wherein the lanes are coextruded.

5. The method of claim 1 wherein the second polymeric material is foamed by utilizing a chemical foaming agent.

6. The method of claim 1 wherein the second polymeric material is foamed by injecting gas.

7. The method of claim 1 wherein the second polymeric material is a thermoset.

8. The method of claim 1 wherein the composite polymeric sheet includes a plurality of lanes comprising first and second materials.

9. The method of claim 8 wherein the lanes comprising the first and second polymeric material alternate.

10. The method of claim 1 wherein the first polymeric material is polypropylene.

11. The method of claim 1 wherein the second polymeric material is an elastomer.

12. The method of claim 11 wherein the elastomer is a polypropylene-based thermoplastic vulcanizate.

13. The method of claim 1 wherein the lane comprising the second polymeric material has a height that is greater than a height of the lane comprising the first polymeric material, each height being measured from a back surface of the respective lane to the top surface of the respective lane.

14. The method of claim 1 wherein the at least one exposed surface of the composite sheet defines a portion of a top surface of the lane comprising the first polymeric material.

15. The method of claim 1 wherein the forming of the lanes and the joining of the lanes is performed concurrently.

\* \* \* \* \*

UNITED STATES PATENT AND TRADEMARK OFFICE
CERTIFICATE OF CORRECTION

| | | |
|---|---|---|
| PATENT NO. | : 7,172,008 B2 | Page 1 of 1 |
| APPLICATION NO. | : 10/666304 | |
| DATED | : February 6, 2007 | |
| INVENTOR(S) | : Brian J. VanBenschoten et al. | |

It is certified that error appears in the above-identified patent and that said Letters Patent is hereby corrected as shown below:

Title Pg, Item (57) Abstract, second to last line, delete "mateial" and insert --material--.

Signed and Sealed this

Sixth Day of May, 2008

JON W. DUDAS
*Director of the United States Patent and Trademark Office*